US010698984B2

(12) United States Patent
Sucilla et al.

(10) Patent No.: US 10,698,984 B2
(45) Date of Patent: Jun. 30, 2020

(54) METHOD AND APPARATUS FOR A MANAGEMENT SYSTEM FOR USER AUTHENTICATION AND PRESCRIPTION REFILL VERIFICATION

(71) Applicant: RXGUARD, LLC, Dover, DE (US)

(72) Inventors: Gregory A. Sucilla, Homewood, IL (US); Robert M. Grohe, Homewood, IL (US)

(73) Assignee: RXGUARD, LLC, Dover, DE (US)

( * ) Notice: Subject to any disclaimer, the term of this patent is extended or adjusted under 35 U.S.C. 154(b) by 563 days.

(21) Appl. No.: 15/328,865

(22) PCT Filed: Jul. 24, 2015

(86) PCT No.: PCT/US2015/042037
§ 371 (c)(1),
(2) Date: Jan. 24, 2017

(87) PCT Pub. No.: WO2016/014964
PCT Pub. Date: Jan. 28, 2016

(65) Prior Publication Data
US 2017/0213010 A1 Jul. 27, 2017

Related U.S. Application Data

(60) Provisional application No. 62/029,118, filed on Jul. 25, 2014.

(51) Int. Cl.
*G06F 21/44* (2013.01)
*G06F 19/00* (2018.01)
(Continued)

(52) U.S. Cl.
CPC ......... *G06F 19/3456* (2013.01); *G06Q 50/22* (2013.01); *H04L 9/3226* (2013.01); *H04L 2209/88* (2013.01)

(58) Field of Classification Search
CPC .. G06F 19/3456; G06F 19/00; G06F 21/6245; G06F 21/34; H04L 2209/88;
(Continued)

(56) References Cited

U.S. PATENT DOCUMENTS 4,958,280 A  9/1990 Pauly et al.
5,907,493 A  5/1999 Boyer et al.
(Continued)

FOREIGN PATENT DOCUMENTS

WO    0186574 A2    11/2001

OTHER PUBLICATIONS

International Search and Written Opinion received for PCT/US2015/042037 dated Dec. 23, 2015.
(Continued)

*Primary Examiner* — Maroun P Kanaan
(74) *Attorney, Agent, or Firm* — Dorsey & Whitney LLP

(57) ABSTRACT

Described is a method and system for the secure management and verification of prescriptions allowing patients, doctors and dispensers to access prescriptions as directed by patients. An example method may include generating a code vector including a series of authentication codes, storing at least one of the authentication codes on a peripheral device, maintaining an indication of a next expected authentication code from the code vector, allowing prescription creation by a user when the peripheral device is detected and determined to be an authorized device, and that the authentication code provided from the peripheral device matches the next expected authentication code, storing a prescription associated with a patient having a patient PIN, wherein the prescription is provided by the user, generating a plurality of refill verification codes associated with the prescription, and authorizing dispensing responsive to receipt of one of the plurality of refill verification codes and the patient PIN.

13 Claims, 9 Drawing Sheets

(51) Int. Cl.
*G06Q 50/22* (2018.01)
*H04L 9/32* (2006.01)
(58) Field of Classification Search
CPC ...... H04L 9/3226; G16H 10/60; G16H 10/65; G06Q 50/24; G06Q 10/10
See application file for complete search history.

(56) References Cited

U.S. PATENT DOCUMENTS

| | | | |
|---|---|---|---|
| 6,055,507 | A | 4/2000 | Cunningham |
| 6,112,182 | A | 8/2000 | Akers et al. |
| 6,157,722 | A | 12/2000 | Lerner et al. |
| 6,278,999 | B1 | 8/2001 | Knapp |
| 6,493,427 | B1 | 12/2002 | Kobylevsky et al. |
| 6,687,676 | B1 | 2/2004 | Denny |
| 6,860,513 | B2 | 3/2005 | Kaufman |
| 7,044,664 | B2 | 5/2006 | Papetti |
| 7,218,395 | B2 | 5/2007 | Kaye et al. |
| 7,426,475 | B1 | 9/2008 | Tangellapally et al. |
| 8,670,991 | B2 | 3/2014 | Kost et al. |
| 8,700,827 | B2 | 4/2014 | Capomaggio |
| 8,861,816 | B2 | 10/2014 | Lang et al. |
| 2002/0052760 | A1 | 5/2002 | Munoz et al. |
| 2002/0095315 | A1 | 7/2002 | Redel |
| 2002/0133376 | A1 | 9/2002 | Fritschen et al. |
| 2003/0018495 | A1 | 1/2003 | Sussman |
| 2003/0074234 | A1 | 4/2003 | Stasny |
| 2005/0216313 | A1 | 9/2005 | Claud et al. |
| 2009/0076849 | A1 | 3/2009 | Diller |
| 2011/0179405 | A1* | 7/2011 | Dicks .................. G06F 8/61 717/168 |
| 2011/0307265 | A1 | 12/2011 | Bannis |
| 2012/0023592 | A1 | 1/2012 | Wilson |
| 2012/0148049 | A1 | 6/2012 | Bellwood et al. |
| 2012/0150561 | A1 | 6/2012 | Carroll et al. |
| 2012/0150563 | A1 | 6/2012 | Carroll et al. |
| 2013/0173280 | A1 | 7/2013 | Denny |
| 2013/0211857 | A1 | 8/2013 | Patch |
| 2013/0231945 | A1 | 9/2013 | Barry |
| 2013/0297333 | A1 | 11/2013 | Timmons et al. |
| 2013/0339043 | A1 | 12/2013 | Bakar et al. |
| 2014/0094965 | A1 | 4/2014 | Silverbrook et al. |
| 2014/0142971 | A1 | 5/2014 | Panagakos |
| 2014/0207686 | A1 | 7/2014 | Experton |
| 2014/0300490 | A1 | 10/2014 | Kotz et al. |
| 2018/0032684 | A1* | 2/2018 | Raja .................. G06F 19/3475 |

OTHER PUBLICATIONS

Lohr, et al., "Securing the E-Health Cloud", Proc. First ACM Int'l Health Informatics Symp. (IHI '10), Retrieved from: http://www.trust.rub.de/media/trust/veroeffentlichungen/2010/10/22/ehealth-tvd_IHI2010.pdf, Jan. 1, 2010, 1-9.

* cited by examiner

METHOD AND APPARATUS FOR A MANAGEMENT SYSTEM FOR USER AUTHENTICATION AND PRESCRIPTION REFILL VERIFICATION

RELATED APPLICATIONS

This application is a U.S. National Stage entry under 35 U.S.C. 371 of PCT Application No. PCT/US2015/042037, filed on Jul. 24, 2015, entitled "METHOD AND APPARATUS FOR A MANAGEMENT SYSTEM FOR USER AUTHENTICATION AND PRESCRIPTION REFILL VERIFICATION", which claims priority to U.S. Provisional Application No. 62/029,118 filed Jul. 25, 2014, entitled "METHOD AND APPARATUS FOR A MANAGEMENT SYSTEM FOR USER AUTHENTICATION AND PRESCRIPTION REFILL VERIFICATION", which applications are incorporated herein by reference, in their entirety, for any purpose.

BACKGROUND

The public relies upon a medical value chain system that integrates doctors, dispensers, and manufacturers of medical products and devices in order to provide many types of health-related products and services. Each group in this value chain adds significant expertise and efficiencies to bring to bear the best possible degree of care at reasonable prices for as many people as possible. Moreover, various mechanisms oversee the practices of each of these groups in order to ensure that each participant is providing products or services that meet or exceed acceptable standards that are established by authoritative bodies, such as the Food and Drug Administration. Various licensing and self-governing associations, such as the American Medical Association, oversee the expertise and competency of our doctors and their ability to exercise sound medical judgment. Dispensers of medical products are licensed and monitored by various authorities to ensure that medications and medical devices are dispensed in accordance both with law and the instructions of the prescribing Health Care Professional (HCP). HCP may generally include physicians, Eye Care Practitioners (including optometrists and ophthalmologists), dentists, oral surgeons, veterinarians, neurologists, psychiatrists, psychologists and all others who are licensed, registered or otherwise permitted, by the United States or the jurisdiction in which he or she practices and is empowered to issue prescriptions or medical diagnoses. Manufacturers must first obtain FDA-approval to manufacture and market medicines and medical devices to the general public.

One element that integrates doctors, patients, dispensers and manufacturers is the prescription. Prescriptions are authoritative records that contain a doctor's diagnosis and/or specific instructions for treatment of a particular patient's diagnosed condition at a specific point in time. Prescriptions are therefore personal and timely, in that a prescription that is good for one individual is not necessarily good, and can be harmful, for another individual or even the same individual after the passage of time. Moreover, prescriptions establish a limitation on the specific dosage, frequency of use, refill amounts, expiration date and other usage requirements or limitations, thereby making the prescription correspond with specific time and application parameters specified by the prescribing doctor.

The prescription most often specifies a medication or medical device intended to address the patient's particular condition as diagnosed by the doctor. The prescription of a particular medicine or medical device presumes both that the product is currently formulated and is currently produced by a recognized manufacturer (or can be produced on site). The prescription further presumes reasonable availability through a recognized source for dispensing. Thus the prescription links together the doctor, the patient, the dispenser and the manufacturer in a prescription value chain. "Dispenser" generally refers to one who prepares and distributes medication, medical devices or medical and/or insurance services to patients as specified by a prescription, the basis for which may either be for-profit or not-for-profit. Other terms that may be interchangeably used in the present context would include without limitation "pharmacy", "retailer", "vendor", "merchant", "point of sale", "seller" and others.

This integrative prescription system has served us well for many decades. Earlier in our history, patients, physicians and pharmacists resided within relatively small communities; they were likely to have known each other personally and to have been able to recognize each other in person. This general familiarity allowed for a system whereby a physician could issue a prescription document to the pharmacist (who at earlier part of our society prepared the medication on-site) via the patient. This traditional system presumed the prescription to be bona fide and that the person presenting the prescription for fulfillment had been examined by a qualified, licensed physician and found to have a particular medical condition that warranted the medication or treatment specified on the prescription document. Seldom was there a challenge advanced as to the legitimacy of the actual prescription document itself, the authenticity of the underlying diagnosis, or the specific information contained within the prescription. Rather, prescriptions have been generally regarded as bona fide medical instructions from a particular, licensed physician for a particular patient concerning a particular medication or for a particular medical supply or device. Upon presentation of a prescription, fulfillment was customarily straightforward.

However, new forms of care delivery (such as HMOs and diagnoses over remote distances via technology) have emerged and the manner by which doctors, patients, dispensers and manufacturers interact has changed greatly from those earlier days. Where once a patient might have been readily recognized by both the prescribing physician and pharmacist—or at least the prescription document presented was presumed by the pharmacist to be legitimate—now prescriptions pass from an HMO physician to a new patient (whom the physician might see only once) who then seeks to have the prescription filled in a distant city or from an on-line dispenser (sometimes referred to as an internet pharmacy). As a result of these changes, the familiarity between the participants in the prescription cycle has declined to the extent that the participants in the prescription system are most often strangers to one another. Yet despite these professional and market changes, the traditional prescription itself has remained essentially unchanged.

Problems such as prescription misrepresentations, prescription misuse and prescription fraud have arisen. Individuals without a legitimate medical condition have nevertheless presented forged prescriptions to a pharmacist in order to acquire certain desired medications. In other instances, individuals with a legitimate medical condition have sought out multiple qualified, licensed doctors to validate their condition and acquire multiple prescriptions in order to obtain a desired medication in a quantity that exceeds the prescribed refill or volume limits of any single prescription. In still other instances, individuals have sought to self-diagnose their ailments and acquire prescription medications without ever having had an original prescription, as has reportedly occurred in on-line purchases of pharmaceuticals. In still other instances, individuals have stolen the identity of licensed medical practitioners in order to submit fraudulent insurance claims. Moreover, there is concern that many imported pharmaceuticals are acquired without a valid prescription being in place.

The intrinsic authoritative value of a prescription has thus declined in this environment. Once a prescription document itself leaves a doctor's office, the doctor does not have the ability to monitor whether the prescription has been dispensed and at what rate, to cancel or otherwise adjust the prescription, or to monitor any fraudulent use of the prescription itself, such as the duplication or forging of information contained on the prescription paper. Moreover, Health Care Professionals prescribe medicines or medical devices for a patient without having the opportunity or capability to review an empirically verifiable prescription history for that patient, because a patient might be under the care of multiple physicians with various areas of expertise, and because the current prescription system does not create a systemic archival record of all prescriptions per individual patient.

Consumer choice is limited and constrained by this dissonance. With the emergence of digital commerce, consumer options have increased dramatically. Consumers today cannot only buy products from traditional brick-and-mortar stores, but from on-line sources, including the manufacturers themselves. Patient interest in such alternative channels through which to acquire medication, medical devices, and medical and diagnostic services has greatly increased due to convenience, service, and price issues. But because dispensing of prescription products requires that a bona fide prescription be presented or otherwise verified prior to dispensing, order fulfillment can be delayed in order for prescription verification to be made. For example, the Fairness to Contact Lens Consumers Act of 2004 (FCLCA) allows for an eight-hour time frame within which prescribing Eye Care Professionals can respond to verification requests made of them by dispensers. In some instances, incompatibility between on-line fulfillment of prescriptions and laws or regulatory requirements has led to estoppels against on-line medical product transactions. At least one state has required that a prescription document be surrendered to a licensed dispenser prior to prescription fulfillment. However, this requirement effectively prevents on-line pharmacies from operating legally within the state.

Businesses that dispense or supply medicines, medical devices, and medical services (such as diagnostic testing) and insurance services to the public have become increasingly concerned about the authenticity of prescriptions, but these same businesses lack a quick, efficient and cost-effective means to verify the legitimacy of a prescription document that has been presented to them. For example, contact lens dispensers are required by the FCLCA to verify a contact lens prescription with the prescribing doctor. Yet as mentioned above, order fulfillment will be slow with any system that utilizes the full 8-hour window for verification allowed by law.

One recent approach to resolve these problems is the use of specialty papers. Specially-made prescription papers bear various physical properties or characteristics that differentiate the prescription paper from normal paper, and thereby enable a ready determination that a particular prescription is a bona fide document. Holographic images, watermarks, security strips (such as are currently found in most recent editions of US paper currency) and other physical property papers have been introduced to enable immediate recognition of the prescription as bona fide. However, if the paper itself is stolen and fraudulent prescription information forged onto it, then the fraud prevention goal of such specialty paper is defeated.

Thus the absence of a reliable and rapid system to verify the legitimacy of a medical or eye care prescription and prescription refills presented for fulfillment is believed to result in higher costs, operational inefficiencies, fraud (including counterfeit prescriptions and doctor shopping), and in some instances, injury or even death (where fraud has led to purchase and use of pharmaceuticals without a doctor's prescription). There remains a need for a method or system to prevent misuse, misrepresentation and fraud of prescriptions and to enable a method or system by which all legitimate participants in the prescription generation and dispensing cycle can reliably ascertain that a particular prescription and each prescription refill are bona fide. There also remains a need for a method or system to enable patients to manage prescription refills separately and individually, so as to increase consumer choice, flexibility to use multiple suppliers using one prescription and to securely verify prescription information to exclude fraud and doctor shopping.

SUMMARY

Example methods and systems for management of user authentication and prescription refill verification are disclosed herein. An example method for securing prescription data may include generating a code vector including a series of authentication codes, storing at least one of the authentication codes on a peripheral device, maintaining an indication of a next expected authentication code from the code vector, allowing prescription creation by a user when the peripheral device is detected and determined to be an authorized device, and that the authentication code provided from the peripheral device matches the next expected authentication code, storing a prescription associated with a patient having a patient PIN, wherein the prescription is provided by the user, generating a plurality of refill verification codes associated with the prescription, and authorizing dispensing responsive to receipt of one of the plurality of refill verification codes and the patient PIN.

An example system for securing prescription data may include one or more processing units, at least one computer readable media encoded with instructions. Upon execution of the instructions by the one or more processing units, the instructions may cause the one or more processing units to at least generate a series of authentication codes, store at least one of the authentication codes on a peripheral device, maintain an indication of a next expected authentication code, allow prescription creation by a user when the peripheral device is detected and determined to be an authorized device, store a prescription associated with a patient having a patient PIN, generate a plurality of refill verification codes associated with the prescription, and authorize dispensing responsive to receipt of one of the plurality of refill verification codes and the patient PIN. The instructions may cause the one or more processing unit to determine whether the peripheral device may be authorized device, at least in part, by identifying a match between the next expected authentication code and the at least one authentication code provided by the peripheral device. The prescription, in some embodiments, may be provided by the user of the peripheral device.

Another example method may include generating a list of authentication codes associated with a user, verifying an identity of the prescribing user by comparing a first authentication code of the list of authentication codes with a seeded authentication code stored on a peripheral device associated with the user, receiving a prescription for a patient from the user, providing a unique, separate refill verification code for the prescription, and authorizing dispensing based at least on receipt of the unique, separate refill verification code.

BRIEF DESCRIPTION OF THE DRAWINGS

The appended drawings illustrate only embodiments of systems and methods described herein and are therefore not to be considered limiting of the scope of the disclosure, which may admit to other equally effective embodiments.

DETAILED DESCRIPTION

Figure 1:
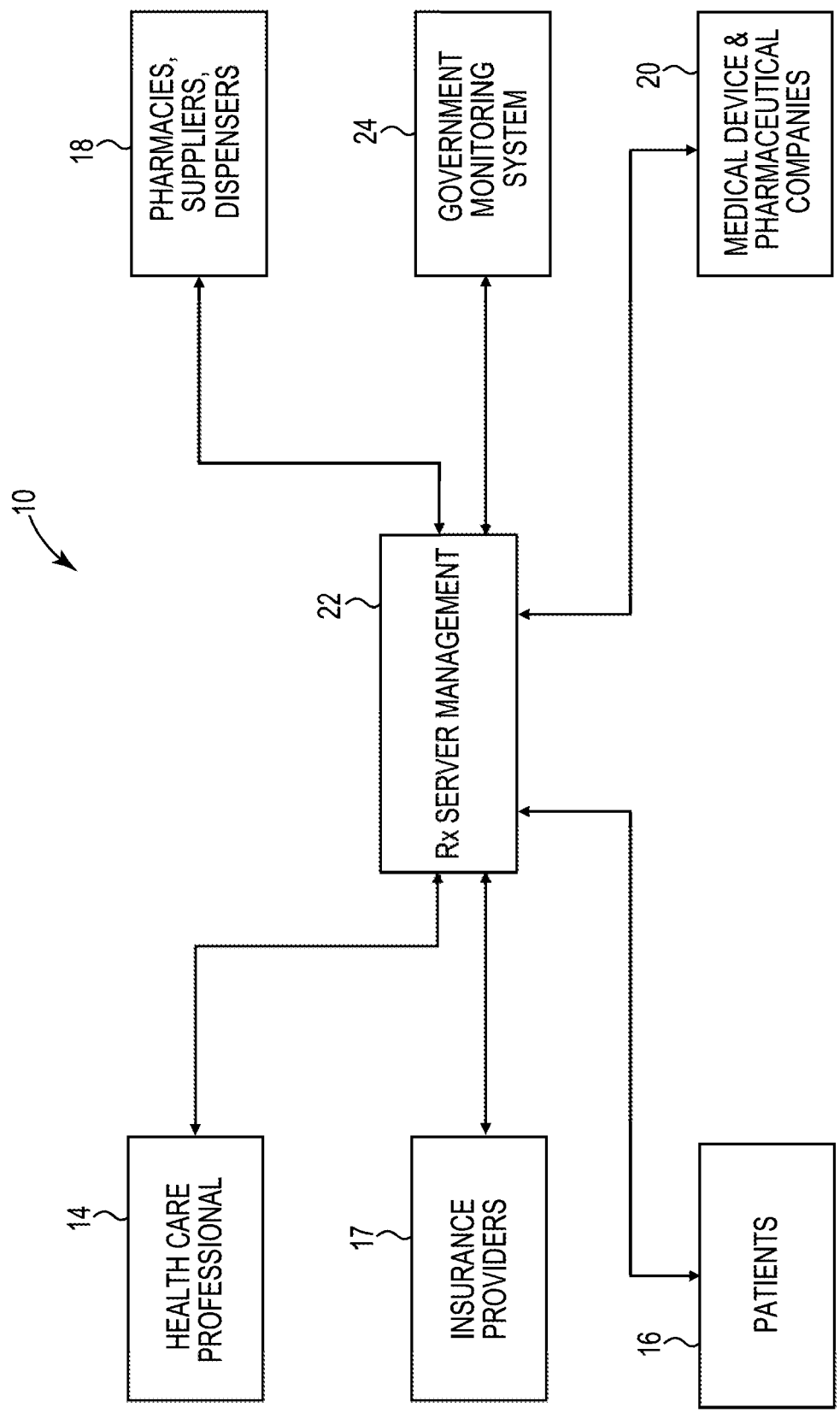
FIG. 1 is a block diagram of an example prescription management system according to an embodiment of the present disclosure.

Whereas the present disclosure may be described in the context of the American Medical Complex, the disclosure may be equally applicable to all other jurisdictions with different licensing and governing bodies. For example, Canadian HCPs may be licensed under local laws and regulated by Health Canada. Australian HCPs may be licensed under Australian law and regulated under the Therapeutic Goods Administration. HCPs in the United Kingdom may be regulated under the Medicines and Healthcare Products Regulatory Agency, From the standpoint of the Health Care Professional, it may be desirable if a prescription management method and/or system is able protect against identity theft and fraudulent use of prescribing powers. It may therefore be desirable that the prescription management method and/or system be able to offer physical and digital security features such that only licensed Health Care Professionals who are registered users gain access to any and all prescription management tools. It may also be desirable that the prescription management system enables physicians to ascertain whether a patient has already been issued a prescription for the same or similar treatment prior to creating and/or issuing a new prescription. It may further be desirable if the system may enable Health Care Professionals to monitor prescription refill fulfillment for their patients, and to remotely amend or cancel existing prescriptions including any or all or its remaining refills.

From the standpoint of the dispenser and insurance carrier, it may be desirable if the prescription management method and/or system may enable a pharmacy, financial services provider, or insurance provider to validate that a prescription and/or its specific refills or claims documents being presented for fulfillment are indeed bona fide prescription refills or documents originating from a licensed physician or medical professional authorized to issue prescriptions or medical or psychological diagnoses. It may also be desirable if the prescription management method and/or system may preclude unauthorized prescriptions or documents containing diagnoses—which nonetheless bear that medical professional's name and likely forged signature—from being used to acquire any medicines, medical supplies, eye care products or insurance or financial services (for which a prescription is required) or to secure approval for fraudulently submitted insurance claims. It may also be desirable if the prescription management method and/or system provides a unique protected access to the system for prescriptions and diagnoses information. A prescription management system may therefore be one in which both the sender and receiver of medical and personal information may interact with complete confidence that each party in the transmission-receipt cycle has been authenticated and approved to handle such information.

From the standpoint of the manufacturer, it may be desirable if the prescription management system archives and processes prescription-related data that allows for HIPAA-compliant marketing intelligence. It may also be desirable if the prescription management system enables secure verification of individual prescription refills so that manufacturers may supply products directly to consumers, whilst being compliant with HIPAA protocols. It may also be desirable for the prescription management system to enable direct entry by authorized users to enter or update catalogue information for products that populate the data fields.

From the standpoint of the patient, it may be desirable if the prescription management system enables for a portable prescription, such that, in addition to their inclusion on a traditional paper prescription, the prescription's refill codes and other prescription data may be downloadable to a laptop, pda, cell phone or a peripheral drive such as a thumb drive. It may also be desirable if each prescription refill and its associated refill verification code may be individually lockable and un-lockable, with a capability to separately send to and grant authorization to different pharmacies, dispensers, suppliers or retailers for verification of that refill and for filling the order for that refill.

It may also be desirable if the prescription management system enables the patient to retain control over each prescription refill via a changeable, unique code of the patient's designation, such as personal identification number (PIN). It may also be desirable if the prescription management system enables the patient remotely to access his or her prescription records and to be alerted as to any changes in or use by others of the patient's prescription information. It may also be desirable if the system maintains a log with access to the patient for all instances of access and use of patient prescription information by any and all users.

Examples of systems and methods described herein may have some or all of the desirable aspects described above.

However, it is to be understood that not all examples may have all, or even any, of the desired features mentioned above. Instead, the desired features are provided by way of illustrating how some examples described herein may have significance to particular users or groups.

Examples of prescription management systems described herein may integrate: a unique security method for read-write access to key system functions and information, a method for registering and verifying prescriptions and their specific refills, a suite of prescription management tools to control prescriptions and a method for verifying prescription refills and receiving a transaction approval code.

Example prescription management systems may be governed by logic (e.g. software) that determines the scope of rights and privileges to enter and utilize the system's access-controlled areas which may include, without limitation, such components as the prescription pads (used to generate a prescription) and other functional modules, databases, product catalogues, and prescription transaction logs. Each registered user is assigned specific access and user rights upon registration that are changeable at the system level upon verified changes to the original registrant's status. It should be recognized that individual registered users may have the same or different access rights as those of other registered users, depending upon various factors.

The example logic governing the system's access-control may be whether the registered user is authorized to have prescribing or other writing powers or whether the user is to have read-only access to the system's features and modules. An HCP's account may have powers to write prescriptions, but not to add or amend any product information. A manufacturer's account may have rights to enter or adjust data in the product database, but not to view patient medical or prescription information or to write prescriptions. A dispenser of medical products or services may have read-only powers and access rights to verify prescriptions, but not to write prescriptions nor to add or amend product database information. A patient/customer may have read-only access to his or her prescription record, the patient's prescription verification codes and the log which records all access to that record, but he or she may have no powers to add, delete or modify entries into the prescription record or the prescription transaction log. The patient may be granted limited write-access to specific information fields related to the patient (such as address, phone number, email and the like) as well as the ability to change the patient pin.

Example systems may execute additional logic steps that may determine whether a registered user's account having prescription writing privileges is limited in the type of prescribing powers that user is to be granted. For example, an Eye Care Professional (ECP) may have prescribing powers for certain product categories, such as contact lenses, spectacles and certain ophthalmic medications, but may not have prescribing powers over other product categories, such as narcotics. Similarly, a particular ECP may have prescribing powers over medical devices such as contact lenses and spectacles, but not over ophthalmic medications.

FIG. 1 is a block diagram of a prescription management system 10 according to an embodiment of the present disclosure. The system 10 may be implemented on a computer, a network of computers, and/or a server, such as the prescription management server 22 that may be accessible to one or more external systems assigned to or maintained by one or more registered users. Example registered users and their local systems may be shown by the other components shown in system 10. Example users and their local system may include, but are not limited to, licensed HCPs 14, patients 16, pharmacies, suppliers and dispensers 18, medical device manufacturers and pharmaceutical companies 20, government agencies 24, and insurance providers 17. The local systems maintained by the registered user may include one or more corresponding software modules that allow for communication with the server 22. The mechanism of access between the registered users' local systems and the system server 22 may be any known mechanism of communication, for example including one or more mechanisms of communication selected from local computer-to-server, manual input into the server, telephone-to-server, and combinations thereof.

Access to the server 22 may be established by connection to a computer network, such as the world-wide-web, including connecting a physical peripheral device, such as a thumb drive, to a local system maintained by a registered user. Protocols for establishing such communications are well known and any known protocol or computer language may be used to implement examples described herein. It should be recognized that any of the communication links established within the system 10 may be one-way communications, two-way communications, or combinations thereof. In some examples, the server 22 may contain a plurality of program modules (e.g. instructions encoded on one or more computer readable media, such as one or more memories) operating interdependently, with one or more of the plurality of program modules corresponding to one or more of the users listed above. Each program module may comprise computer executable commands, instructions, empowerments and authorizations stored in at least one computer readable media (e.g. memory storage device) associated with (e.g. in communication with) a computer.

Accordingly, examples of systems and methods described herein utilize an electronic communication system or network that includes at least one computer server in at least occasional electronic communication with a plurality of local computers over a dedicated or global communications network (such as the internet). An example server system may include, or is in electronic communication with, a memory device that is programmed with a prescription management software program or module that manages the storage (writing) and retrieval (reading) of prescription information on a data storage device, such as a hard disk drive. The same or a different server may include, or be in communication with, memory programmed with an account management software program or module, optionally part of the prescription management software program or module that controls access to and use of the prescription and claims management software program. For simplicity, examples will be described in the remainder of the disclosure with reference only to a single server although two or more servers or other computing systems may be used. It should be recognized similarly, that the program instructions necessary to perform the steps described herein may be combined in a single program or divided into modules in any number of ways known to a skilled computer programmer, and the disclosure is not limited to any one embodiment. However, the program instructions are described herein as being separated into modules.

A local computer at a user location may include at least the common and standard components such as memory, a data storage device, at least one input device and at least one output device. In some examples, the local computer may be equipped with an available interface (e.g. port), such as a USB port, that may allow a user, such as an HCP, to selectively couple a specially-prepared thumb drive or "Unique Key Device" (UKD) to the local computer. The local computer may also include a network communication device for communicating with the server. It is specifically anticipated that the network communication may be wired, wireless or some combination thereof.

Each registered user may be assigned a seeded UKD after registration and various identity-proofing verifications have occurred. Patients 16, however, may not receive a UKD, but may have other privately known identification information available for use with interacting with the system 10. The UKDs, as will be discussed below, may contain unique identifying information for their corresponding user. The unique identifying information may allow for double authentication and may further provide their user with tailored access to various tools of system 10. Access to the system 10 may be limited or denied if a user attempts access without their associated UKD.

A preferred UKD or physical peripheral device may be a "flash drive" or "thumb drive" device, but may also be other types of peripheral devices such as zip drives, portable disk drives, plastic cards with magnetic strip or other component that can store and processes data (such as a credit card or smart card) and the like, that are portable and removable from ports built into the local device(s), and capable of receiving, sending and storing information, whether in encrypted form or not. The physical characteristics of the UKD might take various configurations, but the peripheral device should at least be capable of receiving, storing, and retrieving information with a CPU, whether at the local device or by a CPU at a local device. Example UKDs may have a permanent memory portion that may only be written to a limited number of times (e.g. once), but can be read many times, for permanent storage of UKD and user identification information.

Figure 2:
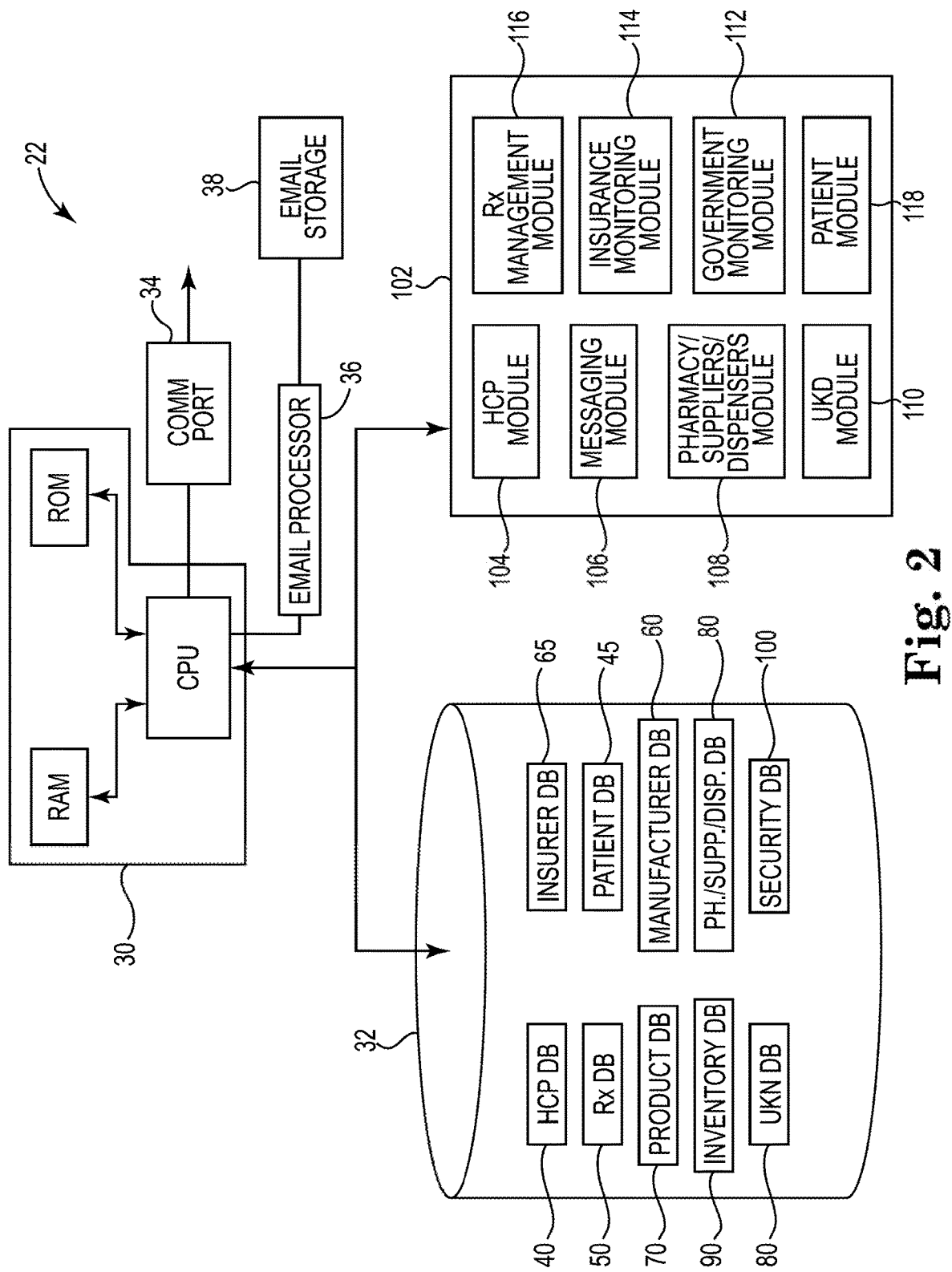
FIG. 2 is a block diagram of a prescription management server according to an embodiment of the present disclosure.

FIG. 2 is a block diagram of the server 22 according to an embodiment of the present disclosure. The server 22 may include one or more processor cores 30, a data base (DB) 32, a communications device/port 34, an optional e-mail processor 36 with e-mail storage 38, and a memory 102. FIG. 2 and the description of FIG. 2 should not be taken as limiting, but rather it is intended as an illustration of the prescription management system disclosed herein. The DB 32 may include one or more devices, for example selected from hard disk drives, compact disk drives, tape drives, or any other storage media. In the illustrated embodiment, the one or more storage devices are shown collectively as DB 32 and having a plurality of databases, including an HCP DB 40, a patient DB 45, a prescription DB 50, a manufacturer DB 60, product DB 70, which may include multiple DBs such that for each medical device manufacturer and pharmaceutical company there is an associated DB, a pharmacy/supplier/dispenser DB 80, an insurer DB 65, inventory DB 90 for each doctor/distributor/retailer, a Unique Key Number (UKN) DB 95, and an electronic security code DB 100 including multiple separate and related vectors of authentication and verification codes. It should be recognized that certain of these databases may be absent in some examples and that the most efficient storage and retrieval of the information may lend itself to other groupings of data in some examples. The various DBs may store information related to the respective associated groups, for example. In some embodiments, information related to products, patients, prescriptions, and etc., may be stored on more than one DB.

The memory 102 may include one or more computer program modules with each of the computer program modules corresponding to one or more of the listed users. In some embodiments, the memory 102 may include an HCP module 104, a messaging module 106, a pharmacy/supplier/dispensers module 108, a UKD module 110, a government monitoring module 112, an insurance monitoring module 114, a prescription management module 116, and a patient module 118. Each of modules may be configured to facilitate and manage interactions between one or more of the listed users. The various computer program modules may interact with one or more of the other modules and access one or more of the databases included in the DB 32 during operation. For example, the prescription management module 116 may interact with the HCP module 104, the UKD module 110, the HCP DB 40, the prescription DB 40, and the patient DB 45 during a session an HCP may have with the system 10. Another example may include a patient logging in through the patient module then interacting with the prescription management module 116, the pharmacy/suppliers/dispensers module 108, the insurance monitoring module 110, the prescription DB 40, the product DB 60, and the patient DB 45 during a session.

Each database shown in FIG. 2 may be used in the prescription refill management system 10 to store and organize information for corresponding listed users. For illustration, some aspects of the description of the system 10 may be framed within the context of a contact lens prescription. This illustration should not be taken to limit the invention to contact lens prescription refill management, but is intended as a detailed example of how system 10 may be implemented. Further, it is anticipated that the present disclosure, including the devices, databases and program modules, are adapted for use not only in eye care (optometry and ophthalmology) prescription management, but as well as for spectacle prescription management, medical or pharmaceutical prescription management, therapy prescription management, and generally for the management of information that is to be maintained in confidence from third parties, but accessible to authorized individuals or entities.

While the content of prescriptions are largely dictated by the health professions or state law, the minimum amount of information generally included in contact lens, spectacles, and medication prescription types is indicated below.

In terms of contact lenses, prescriptions may include: base curve, power (e.g. sphere, and possibly cylinder and axis), diameter, brand/material, name of patient, date of exam, expiration date (usually 1-2 years from date of exam), quantity, and number of refills. This list of information may be stored in the prescription DB 50, for example, and/or the patient DB 45.

Prescriptions for spectacles may include: sphere power (simply listed as 'sphere'), cylinder power (simply listed as 'cylinder'), axis (which always follows cylinder), prism, base, add power (simply listed as 'add'), intermediate power (simply listed as 'int'), lens material, pupillary distance (simply abbreviated 'PD'), name of patient, date of exam, and expiration date (usually 1-2 years from date of exam). This list of information may be stored in the prescription DB 50, for example, and/or the patient DB 45

Prescriptions for medications may include: drug name, dosage, quantity, instructions for use (commonly abbreviated as 'SIG'), number of refills, expiration date, and generic substitution (yes or no). This list of information may be stored in the prescription DB 50, for example, and/or the patient DB 45. While each of the foregoing parameters may be stored in a separate field within the respective DB, it is possible that the entire prescription could be maintained as a single field, text file or scanned image file of a written prescription. Other groupings of prescription data may be used in other examples.

The HCP DB 40 may store registration information about subscribing/enrolled HCPs, including authentication information such as login and password credentials. The patient DB 45 may store conventional demographic information for each patient along with any medical-specific information, such as allergies, currently prescribed medications, physician's notes, etc.—The manufacturer database 60 may allow registration of manufacturers and facilitate communications with those manufacturers. Communications with manufacturers may be useful for example in embodiments having continually updated/upgraded catalogues to drive various other databases, in the instance of having a data information module or for an instance of having a module that enables direct sales by manufacturers, requiring prescription verification. As such, the manufacturer DB 60 may contain conventional contact information for each manufacturer. Log-in specific information may also be maintained for manufacturers that are enrolled in the system 10.

The product DB 70 may include product specific information for prescribed products and over the counter products. The product DB 70 may be used to verify product information. The distributor/retailer DB 80 may allow registration of dispensers and facilitate communications with those dispensers. As discussed, registered dispensers may also require access to the system in order to obtain prescription information that allows them to fill prescriptions for customers having provided them with the necessary patient identification and authorization code.

The security code DB 100 may contain respective entries for each registered user of the system 10. Each entry may contain user identification, a plurality of security codes (e.g., verification codes), PIN numbers, and pointers indicating the specific code or codes that are involved during a transaction. As will be discussed below, each UKD may have a corresponding UKN vector, which may be a list of randomly generated authentication codes used to authenticate respective users. The UKN vectors may be generated by the UKD module 110 in conjunction with the user's UKD and/or user information stored in the security DB 100. The UKN vectors may be generated periodically. The prescription management module 116 may manage the system 10 at an administrative level and also manage the interaction between the server 22 and the various user systems via one or more associated modules. For example, registration of a new user may be performed using the prescription management module 116 interacting with the DB 32. The prescription management module 116 may also manage the interaction between the various modules stored on the server 22 and the various databases included in the DB 32. For example, the UKD module 110 may interact with users and their associated UKDs using security information stored in the security DB 100.

The prescription management module 116 may include a registration function. The registration function may include associated specific arrangements used to verify the professional license information submitted to the system 10 by applicants desiring an account to access the system 10, and a sequence of steps to register licensed health care applicants as user members of the prescription management system, and specific mechanical steps to custom prepare a UKD. To become registered, a user may first submit registration data, and upon its verification the information may then be entered into the server 22 for processing. A new UKD may be placed into communication with the server 22 to receive and store data associated with the user and Unique Key Number(s). These data may vary between types of user. For example, data associated with an HCP may include their DEA number, licensure number(s), name, address, medical practice area, and etc.; Data associated with HCP support staff might include only security access code and personal identifiers but not a DEA number. The system 10 may then process the new UKD and provide the appropriate data, including the first UKN, to the UKD. The resulting seeded UKD may then be ready for user access to the system 10. The term "seeded UKD" may refer to a UKD that includes a UKN, which may be accessed and compared to a vector of UKN's associated with the user on a next log-in.

The prescription management module 116 may also establish prescription writing privileges for registered HCPs. Prescription writing privileges may include one or more capabilities selected from the following, without limitation: creating new prescriptions, editing prescriptions, or canceling one or more of an existing prescription's refills. Other types of writing privileges assignable to a manufacturer include product catalogue management functions, such as the capability to enter new or additional products, remove unavailable products, or amend some relevant aspect of a product already listed in the product database.

The prescription management module 116 may also establish access privileges and read-write privileges for the various types of registered users. The specific scope of access privileges and read-write privileges that a user account receives may be managed by a system administrator of a main database or server or other computing system. The administrator may change or amend these powers or user rights as required. It should be recognized that the administrator may be one or more person(s) or a program that carries out these functions according to instructions maintained by one or more person(s). In any case, the administration of privileges may follow included guidelines that may assure the privileges are given as warranted and authorized. For example, at the system level, an HCP may be required to register and show appropriate authority for prescription writing granted by an appropriate medical practice governing body before the administrator provides the HCP's account with prescription writing privileges within the system.

The prescription management module 116, in conjunction with one or more other modules and one or more databases included in the DB 32, may also generate unique, verification refill codes for each prescription and any associated refills. Each refill may have a corresponding unique verification code, as disclosed herein. A unique, separate and individual prescription refill verification code may be generated for and associated uniquely with each refill of a particular prescription. An HCP's UKD in interaction with a local device and the server 22 may cause either the UKD, local device or the server, or a combination thereof, to generate as many unique, separate and individual prescription refill verification codes as there are refills authorized by the prescription. Where no prescription refills are expressly denoted in the prescription, the system may generate a single refill verification code that is associated with that prescription and the quantity indicated thereon. Accordingly, the unique, separate and individual prescription refill verification code for each refill may be stored in the prescription DB 50, for example. A prescription having five refills, for example, may have five unique, separate and individual prescription refill verification codes. Each of those five refills may have one and only one refill verification code and those five codes would be unique within the patient's prescription record. In some embodiments, the system may be set to not allow any duplication of refill verification codes throughout the system. In some embodiments, the system may be set to allow common use of one or more variables in combination with unique values of other variables, such that unique, separate and individual prescription refill codes result.

One example type of refill verification code may be a composite code that implements a variation of public/private-key cryptography within the code itself. The public key may be a prescription code and the private key may be a UKN of the prescribing HCP, for example. The unique refill verification code thus may include as an example: a prescription code, along with a physician code and a refill code in a random, encrypted combination. This composite code may be distinct from a common Database-Record-Identification-Key—generated automatically and uniquely by a Relational Database Management System (RDBMS)—that may be used to identify and distinguish one prescription record or file from other prescription records or files within the system. A prescription with five allowable refills may have a verification code series including five unique, separate and individual prescription refill verification codes; yet that same prescription may have one and only one Database Record Identification Code. The Database Record Identification Code may not be capable of unlocking any individual prescription refills for purposes of verification.

Verification refill codes may generally be generated in an interactive process between a user, such as an HCP, a user's local device and the user's UKD connected to or in communication with the local device, and/or the server 22. Upon the prescription information being generated and communicated to the server 22, the server may store the prescription information in the prescription DB 50, for example, and may then use one or more elements from the prescription information, together with the next-in-line number from the UKN vector to generate an individual and unique verification code for each refill. For example, the prescription management module 116 may generate the unique verification code(s) using information stored on the HCP's UKD, the security DB 100, the prescription DB 50, or combinations thereof.

As an example, prescription verification codes for a contact lens prescription that includes three allowable refills may be created by combining the next-in-line UKN with particular readings within that prescription, such as:
Refill Verification Code #1: the next-in-line UKN, and the Ocular Dexter axis reading;
Refill Verification Code #2: the next-in-line UKN, and the Ocular Sinister axis reading;
Refill Verification Code #3: the next-in-line UKN, and the Ocular Dexter Base Curve reading;

An example of refill verification codes for a prescription for oxycodone hydrochloride consisting of two refills might be created by combining the next-in-line UKN with other variables, such as:
Refill Verification Code #1: the next-in-line UKN, and the first four digits of the physician's DEA number;
Refill Verification Code #2: the next-in-line UKN, and an internal reference code for oxycodone hydrochloride.

Figure 9:
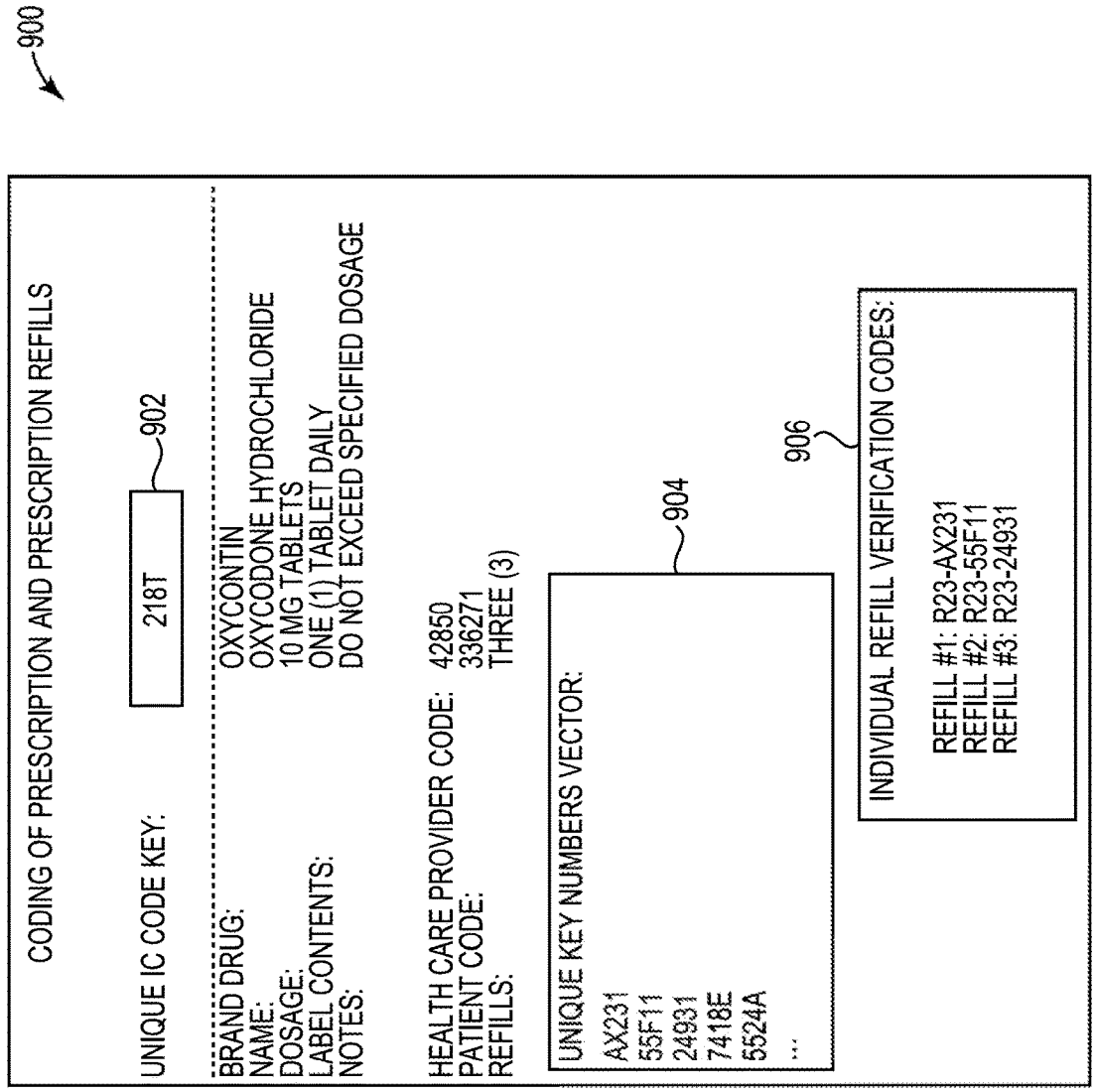
FIG. 9 is an example prescription record 900 in accordance with an embodiment of the present disclosure.

In both instances, because the next-in-line UKN at the local level and that at the server level match, a control against illicit prescription generation may be created. Generally, any element from the prescription information and/or health care provider or user identification may be used to generate the verification code for each refill. In some examples, the verification codes may be generated using data unrelated to the prescription information. Example refill verification codes are shown in FIG. 9.

The HCP module 104 may be used by registered HCPs for creating and managing patient prescriptions, and for patient record analysis. For example, an HCP may access various prescription management tools and interfaces of the HCP module 104 for entering prescriptions and editing existing prescriptions. Once logged into an account with the server 22, an HCP with prescribing powers may submit a prescription (the prescription may include or reference patient identifying information) to the server to be stored by the server into the prescription DB 50 for various purposes including, but not limited to, secure verification of unique, separate and individual prescription refill verification codes.

In accordance with some examples, once a HCP with prescribing powers is logged into an account with the server 22, the user may access a medical diagnosis tool/interface in order to submit patient diagnoses and/or access an insurance claim function of the insurance monitoring module 114 in order to submit claim documents via the server to insurance companies in order to authoritatively document a patient's legitimate condition and services provided for insurance claims purposes. For example, an insured patient may either grant the insurance company access to the diagnosis records in the database or grant the doctor authority to transmit information related to the claim directly to the insurance company.

Upon being approved by the system, the HCP may be granted access to prescriptions pad tools, their respective medication catalogues which populate the data fields, and all other pertinent functional modules that are covered by his or her prescribing power access rights. The HCP may use prescription pad templates to create a prescription, together with unique, separate and individual prescription refill verification codes. The HCP may then submit the prescription, his or her e-signature and patient identifiers to the server for processing as explained herein. In some examples, the server may able to perform a variety of tests against the data existing in a patient's prescription record and/or data being submitted to the patient's prescription record. These tests may include, for example, drug interaction tests and contradictory diagnosis tests. In one embodiment, the server may be programmed to compare both the prescription information and patient identifiers submitted by a doctor against the server databases prior to the system's completion of the prescription registration process. In some examples, this comparison may check for any existing prescriptions for that patient that match the submitted prescription drug, or for existing prescriptions of medications that might trigger possible drug interactions with the medication presently being prescribed. In some examples, if such existing prescriptions exist, the system would alert the doctor with this information. Optionally, the server may then either decline to accept the prescription entry (and therefore decline issuance of unique, separate and individual prescription refill verification codes) and/or to require a doctor's express override and approval to register and issue the submitted prescription despite instances of one or more existing prescriptions that match or pose possible interactions with the drug or device presently being prescribed.

The HCP module 104 may also include patient record analysis tools and interfaces that an HCP may use to review the patient's history, even if such history results from one or more prior visits with different HCP[s]. The patient record analysis tools may allow the HCP to visualize changes to one or more of a patient's physical characteristics, e.g., various eye measurements and test results, over time so that trends may be more readily identified. The patient record analysis tool may access one or more records in the patient DB 45 in order to perform any desired analyses. The patient record analysis tools may also allow the HCP to compare a patient's test results and conditions to various cohort groups to compare and contrast a patient's condition with a large population. The patient record analysis tools and interfaces may also be accessible by one or more of the other program modules, such as the insurance monitoring module 114 and the government monitoring module 112. The HCP module may also notify HCPs in instances where a discrepancy is detected between a particular medication or medical device as recorded on the prescription and that which is provided to the patient in fulfillment of a prescription refill.

The messaging module 106 may manage messages generated by the prescription management system 10 that are to be provided to the various users. For example, prescription details may be sent to a patient or an HCP, and error messages may be provided to intended users. The messaging module may utilize the email processor 36 and store sent and received emails in the email storage 38, for example.

The pharmacy/suppliers/dispensers module 108 may provide the functional modules and interfaces used by the listed users. A pharmacy, supplier, or dispenser may be registered with the system 10 and may be assigned read-only rights to access-controlled areas and controlled information, such as the manufacturer DB 60, the pharmacy/suppliers/distributor DB 80, the product DB 70, and the prescription DB 50. Thus the dispenser may read prescription and prescription refill information, but cannot write to these fields. As a first step to access specific prescription and prescription refill information, the dispenser may first be authenticated by the server as a registered user. In some examples that dispenser, pharmacies, retailers, suppliers and the like utilize a UKD that may be prepared with specific information as previously described. However, system access is a necessary but not sufficient condition for a dispenser to access any prescription information. Access to specific prescription information requires the dispenser to provide both a refill's unique, separate and individual prescription refill verification code and a patient identifier, each uniquely associated with a particular patient, prescription and refill. In this regard, these users interact with the system in order to be authenticated as approved, registered users, and to present a public-private key combination to enable read-only functions regarding specific prescription information.

The pharmacy/suppliers/dispensers module 108 may also provide registered users access to HIPPA-compliant business information that may be used for general and directed marketing campaigns and other business development. In some embodiments, data may be made available in a randomized, anonymized manner for analysis and manipulation by one or more of the registered users. Registered users in this setting may not include patients, however.

The insurance monitoring module 114 may provide insurance companies with an interface for managing and monitoring patient data and prescription information. Additionally, the insurance monitoring module 114 may provide input forms for HCPs to provide requests for treatment approval and for augmenting requests with subsequent comments. The insurance monitoring module 114 may also allow insurance companies to submit treatment regimen protocols that they deem to be best practices. Forms and information regarding registered insurers may be stored on the insurer DB 65.

The government monitoring module 112 may provide access to the various databases stored in the DB 32 for monitoring by various government agencies. For example, the DEA may access the DB 32 in order to monitor for fraudulent narcotic prescriptions and usage. Other government agencies may be able to access the various databases for medical research and the like.

The patient module 118 may be a portal where patients register and provide their demographic information. Patients may further be able to manage their user log-in and password information, and further add/change their PIN numbers used to unlock refill verification codes so that a pharmacy, for example, may provide a refill from an associated prescription. Additionally, patients may be able to access the patient DB 45 to view their medical history including explanatory notes, and access insurance forms included in the insurer DB 65. Patients may be able to register their products for warranty purposes. Patients may also be able to authenticate prescribed medicines and medical devices, and obtain a Certificate of Authenticity. Products may be authenticated upon the patient entering an approval code sent by the system to and received by the retailer upon verification of the refill verification codes, and one or more product/packaging serial numbers obtained from the product sent or given to the patient. For example, if a patient orders contact lenses via an internet company, upon receipt of the contacts, the patient may be able to enter the patient module 118 and provide the required information to determine if the received contacts are bona fide and authentic brands and products made by a specific manufacturer The UKD module 112 may send and receive data to user's UKD while the user is logged into the system 10 for a session. The UKD module 112 may determine if there is a valid UKD at a user's local system and further determine if a UKN matches a corresponding UKN associated with that user's UKN vector. The UKD module 112 may also provide the next-in-line UKN from a user's UKN vector during a user's session. The next-in-line UKN may replace a previous UKN any number of times during a user session.

In some examples, prescribing powers are configured into the system and are accessed by use of a user's UKD. The HCPs who can be authenticated at security levels required by the system (such as with a verified, registered UKD) may enter prescription pad or other access-controlled areas based on the presence of a valid UKD. Moreover, the user may only be able to use those prescribing powers that are pre-authorized and programmed into the system's database (s) at a time of registration or as periodically updated or otherwise adjusted. The UKD may be prepared at the server level of the system before being sent to and used by HCPs, for example. In some examples, a UKD may be inserted or otherwise connected to the server that may encode the blank key with both "write-once-read many" variables, and "write many-read many variables". Upon completion of this device preparation, the UKD may then be sent by the server to the user associated with the registered account by certified, registered express mail or delivery by other common carriers. The user may then activate the key upon insertion into a local device and in interaction between the local device and the server.

During the registration process, the system may store pertinent user identification information into the UKD, which identification information might include, without limitation, the doctor's (or other user-type): name, Drug Enforcement Agency (DEA) license numbers, electronic identification number (EIN), electronic signature, office address(es), telephone number(s), and the like. The customization process may also include seeding of the UKD with data or a program for authenticating the origin of the UKD and/or its content. Example origin authentication schemes may include the use of time-variant or message-variant parameters that may uniquely be stored or determinable by the UKD and by the server in a manner associated with the user account identified by the UKD. For example, a user may attempt to log into the main server using a local computer with a network communication link, such as the internet, to the server. The user also inserts his UKD, which may for example be implemented using a drive such as a thumb drive, into the USB port of the local computer so that the information (or at least a portion of the information) on the UKD is shared with the server to uniquely identify the user. Further, the UKD may be encoded with one or more numeric or alphanumeric codes as identification marks unique to that particular device (such as a serial number). The server may scan for these marks in order to identify the UKD and to establish that the UKD is a device registered with the system.

Examples of UKD may be physical, removable, computer peripheral devices that may be auxiliary to the user's local computer and which may contain certain programming and data that enable the main server, in association with its database of authorized users, to uniquely identify and verify the user. In turn, the identification of the user may allow for authenticated entry to and use of access-controlled areas of the prescription management system according to the user's privileges as explained above. In some examples, two broad data areas may be provided on the UKD: a fixed data area and a variable data area. The fixed data area may include such codes as a model number, unit registration number or serial number, user registration number, doctor name, DEA license numbers, doctor EIN, business address(es), telephone number(s), type of prescribing powers authorized to the user, and/or any other information deemed helpful in distinguishing between multiple HCP users. Variable data may contained in the variable data area may include various codes, as herein described. A Unique Key Number (UKN) may be a numeric variable, an alpha variable, or an alphanumeric variable from a vector of such variables that is uniquely associated with a particular user and with a particular UKD. A UKN may be a function in an authentication process or in a verification process.

During an example process to gain entry to access-controlled prescription areas, the system presents two security levels that must be satisfied. First, the system may scan the UKD (a) for unique identification marks that evidence the device is registered with the system and (b) for the UKN currently stored on the UKD. If the identification marks match those respective data fields stored in the server's memory and if the UKN sent to the server from the user's UKD and local system matches the number next expected by the server, the first security challenge may be satisfied. Second, the user may be required to provide a correct user name and password, which should match those stored in server memory as being associated with the same particular user and user's account. Upon verifying these security inputs, the system may admit the user to the system in a manner consistent with the user's access privileges and read-write privileges.

It some examples, the server may generate a vector of UKNs (e.g. using a Unique Key Number generating algorithm or algorithms uniquely associated with a particular user's account and a particular UKD) and transmit a new UKN to the UKD for storage in the UKD. The vector of UKNs may be stored in the system, and may only be securely accessed by the system during a user's session. In some examples, the vector of UKNs may be encrypted and stored behind a privileged partition. The system may remotely replace these UKN's in the UKD randomly and/or at some frequency during the user's session. At a minimum, the system may have made at least one replacement of the previous UKN scanned for during log-on with a next-in-line UKN from the user's UKN vector. The system's pointer sets this replacement UKN as the next-expected number to be identified by the server at the user's next session or at periodic, random checks by the server of the UKD during a session. The UKD may thus be re-set to allow the user either to submit additional prescriptions during the same on-line session or to log off and re-access the server at a later time.

The significance of these matching numbers is that an attempted security breach may be detected at any instance whereat: (1) the UKN actually transmitted by the specific UKD to the server does not match the next in line UKN expected by the server from that UKD; (2) the UKN received by the server is not associated with the user's UKD or is otherwise an invalid number; or (3) the received UKN has already been used during a previous transaction between that UKD and the server. Upon detecting a possible security breach, the system may be designed both optionally to lock out the current user from some or all functional areas of the system and, optionally, remotely to disable that UKD currently in use. Appropriate messages (that report the attempted security breach and actions taken by the system) optionally are sent both to the specific local device and to the registered user according to their contact information upon detection of any attempted security breach, as well as to any relevant government authority.

In operation, a doctor makes an entry into this or a similar database after completion of an examination. The entries may be typed into a local computer in the doctor's office that is connected or connectable to the server, or, in some examples, directly into a handheld computer device that communicates directly or indirectly with the local computer or server. The software interface for entry of the data may be of any known style, including freeform entry, delimited text, drop-down menus, defined field entry, and combinations thereof. It should also be recognized that certain information (such as the date of examination) might be automatically provided by the handheld computer, local computer or server. While it is anticipated that the doctor will desire to maintain a database similar to that shown, specifically including the patient name and the specific prescription, the existence of a stored database at the doctor's local computer is not necessary in all examples. In fact, the examination information may be directly provided to the server through a connection to a website that contains the entry interface. In this latter scenario, the local computer may not require any specialized software, and just software for connection to the server, such as a web browser.

To submit a prescription refill to a supplier/dispenser/pharmacist 18, a patient may provide a pharmacist a refill's unique, separate and individual prescription refill verification code (the "public key"), and the patient's private patient identifier (the "private key," such as a password), which may be provided through a customer keypad located at the dispenser. The pharmacist may provide this information to the prescription management system 10 via the pharmacy/suppliers/dispensers module 108. The dispenser or pharmacist may thus be provided with a composite code that might include a prescription code, a doctor code, a specific refill code, or another code or codes, each or severally of which in tandem comprise the composite "public" key. Along with a specific refill's verification code, the prescription and doctor codes have been revealed publicly in a transaction. The remaining verification codes and the patient's private PIN remain hidden and protected. Knowing only one element of the unique, separate and individual prescription refill verification codes does not allow retrieval of any system information nor does it allow for the "unlocking" of other refills comprising the prescription's allowable refills. Therefore, no utility is gained by learning a given refill's verification code by itself. Generally, only the patient possesses all pieces of all the verification codes at any given point, which by design may give the patient full control over each and all prescription refills, and the prescription record itself. With the exception of the issuing physician, no third-party access to the prescription record may be made without submitting to the system an appropriate unique, separate and individual prescription refill verification code, along with the patient PIN. Moreover, a bona fide verification code may not be used to access other prescription records, either for the patient from whom a valid verification code and pin has been received or for a different patient.

The patient identifier may be associated with the patient-specific portion of the prescription and may be a patient PIN, part of the patient's social security number, and alphanumeric or entirely alphabetic name or code associated with the patient; this portion of the verification code might also be encrypted or not. The patient identifier may be used only to control access to patient refills/patient information and may not used by the patient in any other manner, such as to log on to the system. A separate patient username and password may be used to log on to the system to permit patients to review their own information. The patient identifier is controlled and changed at will by the patient via access to and interaction with the system.

The unique, separate and individual prescription refill verification codes, along with the prescription, may be provided for delivery to the patient at time of prescribing and/or are available to the patient via on-line access. The method may allow for the server to generate the verification codes and transmit them to the UKD interacting with local devices, or to generate the refill verification codes by interactivity between the server, the UKD and the local device. At some time after prescription data is stored in the computer, access to and management of the unique, separate and individual prescription refill verification codes may be provided upon receiving a request containing a requester's identification, the patient's identification, and the refill's verification code associated with the patient identification. The method may further comprise verifying the identity of the HCP sending the prescription information. At a later time, a request may be received from the patient via a dispenser/retailer wanting to purchase a quantity of products in accordance with the associated prescription. Conventional prescriptions may comprise product identification, the number of allowed refills, the verification code vector, the expiry date and other pertinent information.

In some examples, the system may issue to the dispenser a verification or transaction approval code which evidences both that a prescription (re)fill verification was sought at a specific time and date, that the specific refill was determined by the system to be verified and that the transaction is approved. The approval code may be generated by the server in association with the specific prescription (refill), the requestor, and the patient; the approval code may be stored in databases at the server, at the local device and/or at the Unique Key Device. Authorized users would access the approval code in order to verify compliance with pertinent laws, to evidence a verification attempt, and any other such matters to evidence the transaction.

In some examples if the number of remaining refills requested is less than the allowed number of refills, the prescription's expiry date has not passed, the requested refill(s) does not exceed the number of refills determined by the doctor for dispensing at any one time, and/or the refill verification code exists, has not been previously used, and is associated with a particular patient identifier, then the system may approve the transaction for that particular refill or refills, the approval code(s) may be generated, stored and transmitted to the UKD as discussed above, and the dispensing is fulfilled. In some examples, the server may track each refill's verification code and disable each code after its first use to obtain a refill associated with that code. In some examples, the number of allowed refills recorded in the memory of the computer may be decreased by the number of products dispensed to the patient. In some examples, the system may track the prescription's expiry date.

In some examples, if the quantity of products requested is greater than the allowed number of refills, the prescription's expiry date has lapsed, the requested refill(s) exceed the number of refills determined by the doctor for dispensing at any one time, and/or the verification code has already been utilized, does not exist or is not associated with a particular patient identifier, then the system may decline approval for the transaction for that particular refill or refills and the purchase may be denied.

In some examples, the system may include set points that may only authorize refills in number and at a pace in accordance with doctor directions or that are in accordance with professional standards and practices of the pharmacy profession.

Optionally the system may alert the doctor, relevant government entities and the patient upon detecting prescription access using a previously used, non-existent or non-associated verification code. Further, when the number of allowed refills reaches a patient refill notification set point, then the patient and/or doctor may be notified, such as by e-mail. The patient and the doctor might each have direct and independent access to the prescription record in order to determine the status of prescriptions and verification codes.

It is anticipated that the present method will be particularly well-suited where the product description in the prescription is selected from contact lenses, spectacles, ophthalmic medications, pharmaceuticals, medical equipment and medical supplies. It is also anticipated that the prescription provided to and stored in the computer may include a product description and a prescription expiration date. In some examples, the method may deny access to the prescription at a time following the prescription expiration date. Additional optional features include notifying the patient of the amount of time between the current date and the prescription expiration date and/or notifying the doctor that the prescription expiration date has passed.

A request from a doctor may be submitted to the computer for access to the prescription for a given patient identification, wherein the request includes the patient identification and the associated verification code(s). While the submission of the prescription to the computer may be handled in any known manner, in some examples, a laptop device, a tablet device, a handheld device or other personal data assistant (PDA) for in-office use may be used. Manual entry through a computer keyboard and the like can be equally effective.

An example system may include an input device for receiving a prescription from a doctor for a specified patient; an algorithm module (e.g. software, such as executable instructions encoded on one or more computer readable media accessible to at least one processing unit that, when executed, may cause the at least one processing unit to perform certain functions) that may be used to generate individual refill verification codes; a memory for storing verification codes in association with the prescription, its refills and the patient; an output device for outputting the verification coded for the specified patient and prescription; and at least one processing unit (e.g. a processor) for verifying prescription refill codes and approving prescription refills upon receiving a request containing the patient name, the associated verification code(s) and the private key. The processor may further be for authenticating the identity of the doctor from which the prescription is received. The system may be programmed (e.g. using executable instructions encoded in one or more computer readable media such as a memory) to perform functions described herein, such as verifying and approving prescription refills, authenticating the identity of the doctor, and/or generating verification codes.

Example systems may include without limitation user authentication, prescription generation, management control, and verification subsystems that relate to:

(a) the creation, issuance, storage and processing of prescriptions (e.g. for pharmaceuticals, medical devices and the like) in which individual prescription refills are:
  (1) Separately, individually and securely created;
  (2) Separately, individually and securely assigned verification codes; and
  (3) Separately, individually and securely locked, unlocked and approved by the patient for use by pharmacies, suppliers, dispensers and others for purposes of prescription refill verification and product order fulfillment;

and (b) controlled-entry by and authorization of patient-authorized HCPs, suppliers, pharmacies, insurance providers and others along with certain tools to view, process, verify, authorize and fulfill prescriptions and individual prescription refills authorized and presented for fulfillment by a patient.

Figure 3:
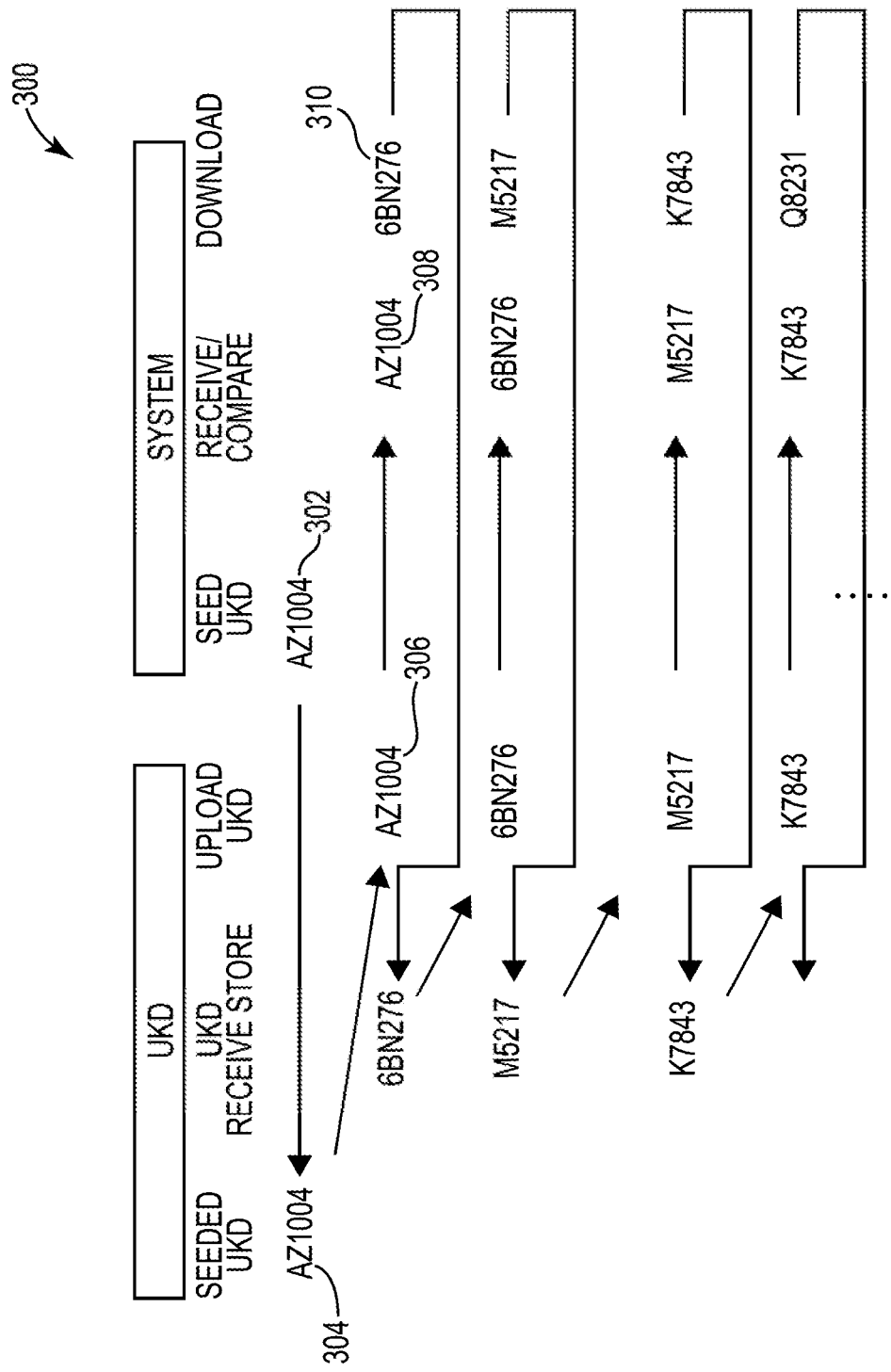
FIG. 3 illustrates a send-receive sequence between a server and a UKD in accordance with an embodiment of the present disclosure.

FIG. 3 illustrates a send-receive sequence 300 that may occur between a prescription management system and a UKD in accordance with an embodiment of the present disclosure. A seed UKN 302 may be seeded into, e.g., provided to, the UKD at a time of preparation of the UKD for a registered user, for example. The seeded UKN 304 may have been stored on the UKD by the server 22 in response to a user registration process performed using the prescription management module 116 and may be the same UKN as the seed UKN 302. The seeded UKN 304 may be a first or next-in-line UKN in a UKN vector generated by the UKD module 110 of the server 22, for example, such as the seed UKN. Alternatively, the seeded UKN 304 may have been provided in a previous user session. Upon the user's use of the UKD, the seeded UKN 304 may correspond to the next-in-line UKN 306 in the UKN vector associated with the user and stored by the server 22 in the user's DB, such as the HCP DB 40. The server 22 may scan the user's UKN vector for the UKN 306 and compare the UKN 306 to the database containing the UKN vector. If the comparison returns a positive result, then a log-in step for the user may be satisfied. Additionally, the UKD module 110 may provide the next UKN in the UKN vector, such as the UKN 310, to the user's UKD. The UKN verification may occur any number of times while a user is logged into the server 22. For example, the UKN verification may occur once a minute while the user is logged into the server 22. Each time the UKN is verified, a next-in-line UKN from the user's UKN vector may be provided to the user's UKD in preparation for the next verification process.

Figure 4:
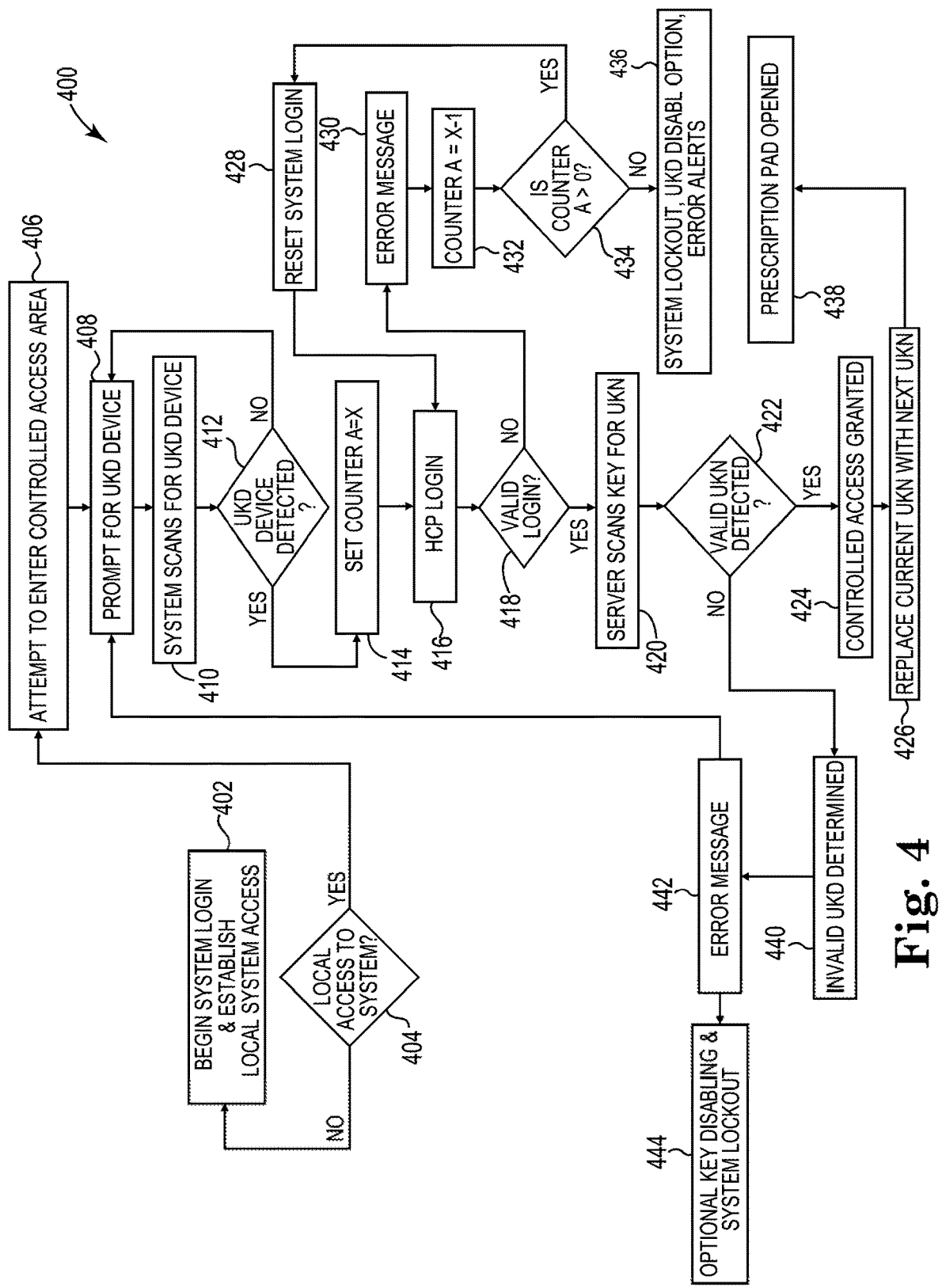
FIG. 4 is a flow diagram of a login and authentication process in accordance with an embodiment of the present disclosure.

FIG. 4 is a flow diagram of a user login and authentication process 400 in accordance with an embodiment of the present disclosure. The process 400 may occur when a user attempts to log into a prescription management system, the system 10 for example. For example, an HCP may attempt to log into the prescription management system 10 to monitor a patient's current prescriptions and/or add a new prescription to a patient's file. Another example may include a pharmacist logging into the prescription management system 10 in order to fill or refill a patient's prescription. However, the process 400 may be the initial log-in process for any and all registered users, such as pharmacists, manufacturers, suppliers, patients, government officials, etc. The process 400 may be disclosed in the scenario of an HCP logging into the system in response to a patient visit for illustrative purposes only. When a patient visits an HCP's office, the HCP may determine that a prescription is necessary. To begin a session with the prescription management system, such as the system 10, at step 402, an HCP may log into the system from a local device using their user ID and password. The user ID and password referred to in the step 402 may be a local password and user ID, which may be different than the HCP's prescription management system-specific password and user ID, which may also be required for the process 400. This log-in sequence may provide the user with access to the HPC's local computing system/device, for example. If the system is unable to verify the user's ID and password, the system may revert back to step 402 to provide additional log on attempts to the HCP in accordance with the local system settings. With local access to the system established, at step 406, the HCP may attempt to access restricted or limited areas of the system using various interfaces of the system. These areas may include access-controlled prescription management and processing functions available for use only by those licensed and registered HCPs with prescribing authority, including medical doctors, medical professionals and Eye Care Professionals whose credentials have been authenticated and become registered users. Further, these areas may be limited to only those functions to which the user may be entitled and which may be programmed into the system and the user's UKD upon initial registration with the system.

To proceed to the desired secure areas and access their corresponding functions, at step 408, the HCP may be prompted to provide their UKD to a connection, e.g., port, of the local device. At the step 408, the system may also prompt the user to "INSERT KEY DEVICE," for example, into the appropriate port location of the local device and to press or select "ENTER," for example, or other designated keyboard key to signal to the system that the UKD is connected.

At step 410, the system may then scan the local device connection to attempt to detect the presence of the HCP's UKD. If it is determined at step 412 that no UKD is detected, the system may revert back to the step 408 in order to prompt the user to insert their UKD in the appropriate port. Upon detecting the presence of the UKD in the designated port, at step 414, the system may set a counter to a pre-set value. At step 416, the system 10 may require the doctor to log in using their system-specific user ID, password and optionally answer a challenge security question. If the user log in is not validated by the system at step 418, an error message may be sent to the local device at step 430, and the counter may be decremented by one at step 432. At step 434, the system may then compare the current value of the counter to zero. If the current value of the counter is determined to be greater than zero at the step 434, the system may proceed to step 428 to reset the log-in information. The system may then request the user to re-enter their log-in information at the step 416. However, if the current value of the counter is determined to be equal to or less than zero at the step 434, the system may proceed to step 436 to initiate a user lock out and optionally remotely deactivate the UKD. Further, the system may alert the HCP's office, the HCP directly, and/or relevant government agencies as to a possible attempt to breach the system.

If the HCP login is determined to be correct at step 418, at step 422, the system may then scan the UKD for both its fixed signature registration code(s) and the variable (initial or next-in-sequence) UKN identification codes. Additionally, at step 422, the system may compare the detected values against the values associated with this HCP stored in the system's database, such as the database 32.

The system, at step 422, may then determine if the UKN is the valid, next-in-line number associated with the particular UKD. If the server does not detect the presence of the codes or if the codes detected do not correspond to values contained in the server database at the step 422, the server may determine that the UKD is an unauthorized device at step 440, and may issue an error message, such as "INVALID KEY" or the like at step 442. An optional system lockup and key disabling function may result at step 444. The system may also be configured to notify user contact information (e.g., the HCP's office, cell phone, pager, or email) and appropriate governmental authorities of an illicit access attempt. Alternatively, the system may revert to the step 408 to prompt the user to insert the UKD. Upon the user reinserting the UKD, the system may rescan the UKD for the UKN according to the step 410.

If it is determined that the UKD signature codes and the next-expected UKN correctly match those stored by the system at the step 422, the system may proceed to step 424 to grant the HCP entry to the restricted areas they have been granted access. Further, at step 426, the system may replace the UKN on the user's UKD with a next-in-line UKN from the user associated UKN vector according to the sequence 300. The system may then proceed to step 438 to grant the HCP access to those prescription management system's controlled-access areas and functions to which the user has been pre-authorized during the registration at step 438. While the process 400 is disclosed to follow the processing of steps depicted in FIG. 4, the order of some or all of the steps may be performed in various other orders and the order shown in FIG. 4 should not be considered limiting.

Figure 5:
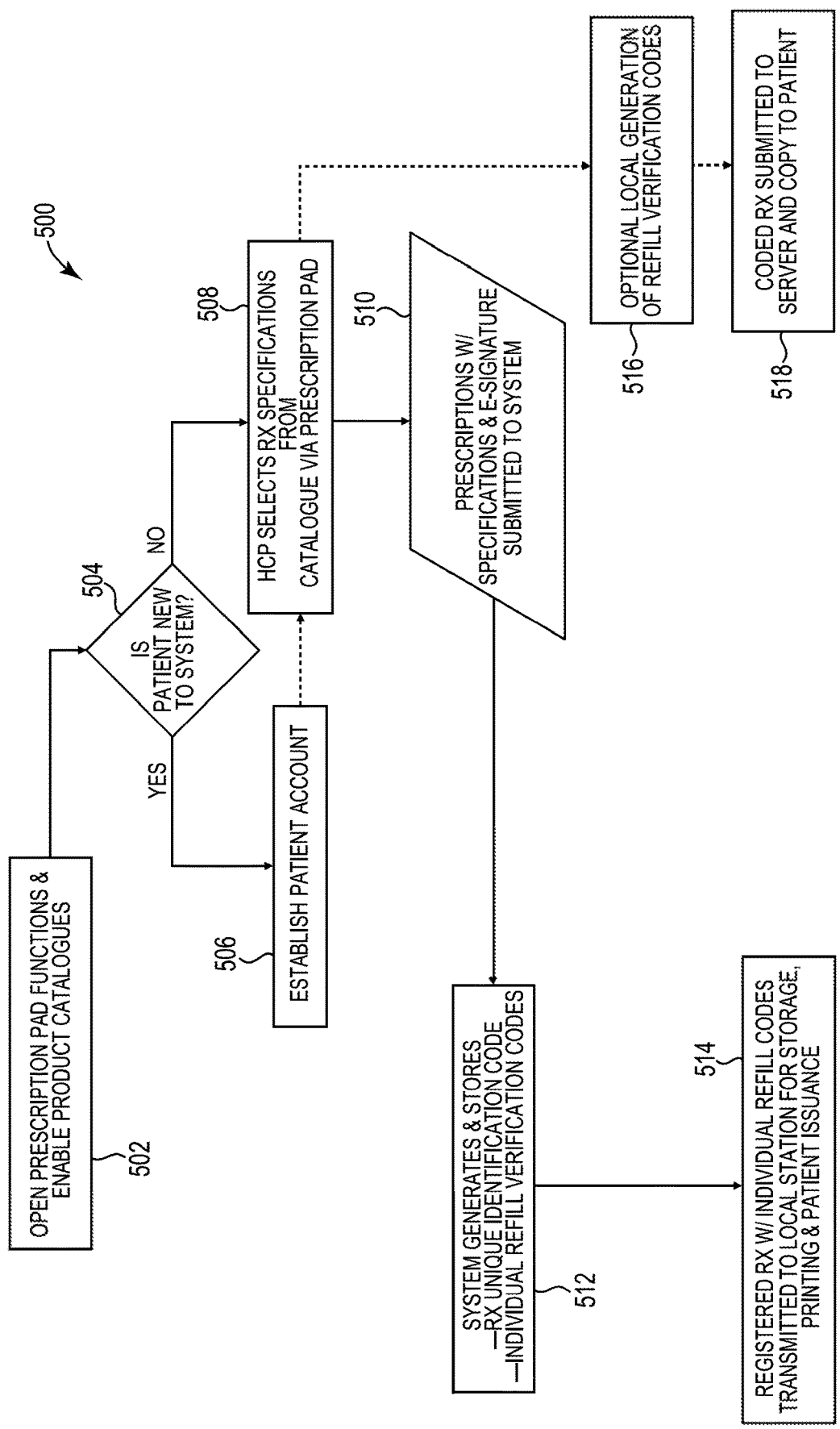
FIG. 5 is a flow diagram of a prescription generation and refill verification code generation process in accordance with an embodiment of the present disclosure.

FIG. 5 is a flow diagram of a prescription generation and refill verification code generation process 500 in accordance with an embodiment of the present disclosure. The process 500 may generate a prescription and create unique, separate and individual verification codes for the initial prescription fill and each refill that may be provided with the prescription. At step 502, the prescription management tool kit(s) and prescription templates to which a user is pre-authorized to access may be opened and the appropriate product catalogues may be opened to populate the prescription options. At step 504, the system may determine if the patient is a new patient. If the patient is determined to be new at the step 504, the system may proceed to step 506 to direct the user to establish new patient information. If, however, the patient is determined to not be new at step 504, the user may be allowed to proceed to step 508 in order to select the necessary prescription information from catalogues included in the system 10, by a manufacturer or insurance company for example. Subsequently, the prescription may be generated and unique, separate and individual verification codes may be assigned to each refill. In one embodiment, the system may proceed to step 516 to generate unique, separate and individual refill verification numbers at a local system, which may then be uploaded to the system along with a hard copy or other form of copy of the prescription and prescription refill verification codes to the patient at step 518. However, in some embodiments, the system may proceed from step 508 to step 510 so that the prescription information and an HCP's e-signature is provided to the system 10. At step 512, to the system 10 may generate the unique, separate and individual prescription refill verification codes, in interaction with the user's UKD and the local device. At step 514, the system may transmit the unique, separate and individual prescription refill verification codes to the local station for providing to the patient.

Additionally, at the step 512, the information may be submitted to the system in order to make prescription information and individual prescription refill codes available for authorized access and verification. In this embodiment, a unique refill verification code may be generated at the server for each individual refill, which may be performed by the prescription management module 116, for example. Each verification code in this embodiment may be a composite alphanumeric code including one or more UKD fixed variables, a UKN or other numbers sent by the system to the UKD, and elements from one or more variables associated with the particular prescription.

Once the system has processed the codes, at the step 514, both the prescription and all associated codes may then be transmitted to the local device for storage, printing and transfer to the patient. If the local device has a continuous connection to the system, for example through a single on-line session over a global computer network, the entered prescription and patient identification may be immediately, periodically, upon command or upon any other basis submitted to the server. Optional batch submission of prescription and patient identification may be practiced regardless of the characteristics of the server connection, but is anticipated to be used mostly with dial-up modem service, person-to-person or person-to-computer telephone systems, and the like. Any number of prescriptions may be entered into local device before sending or submitting at the step 510.

Figure 6:
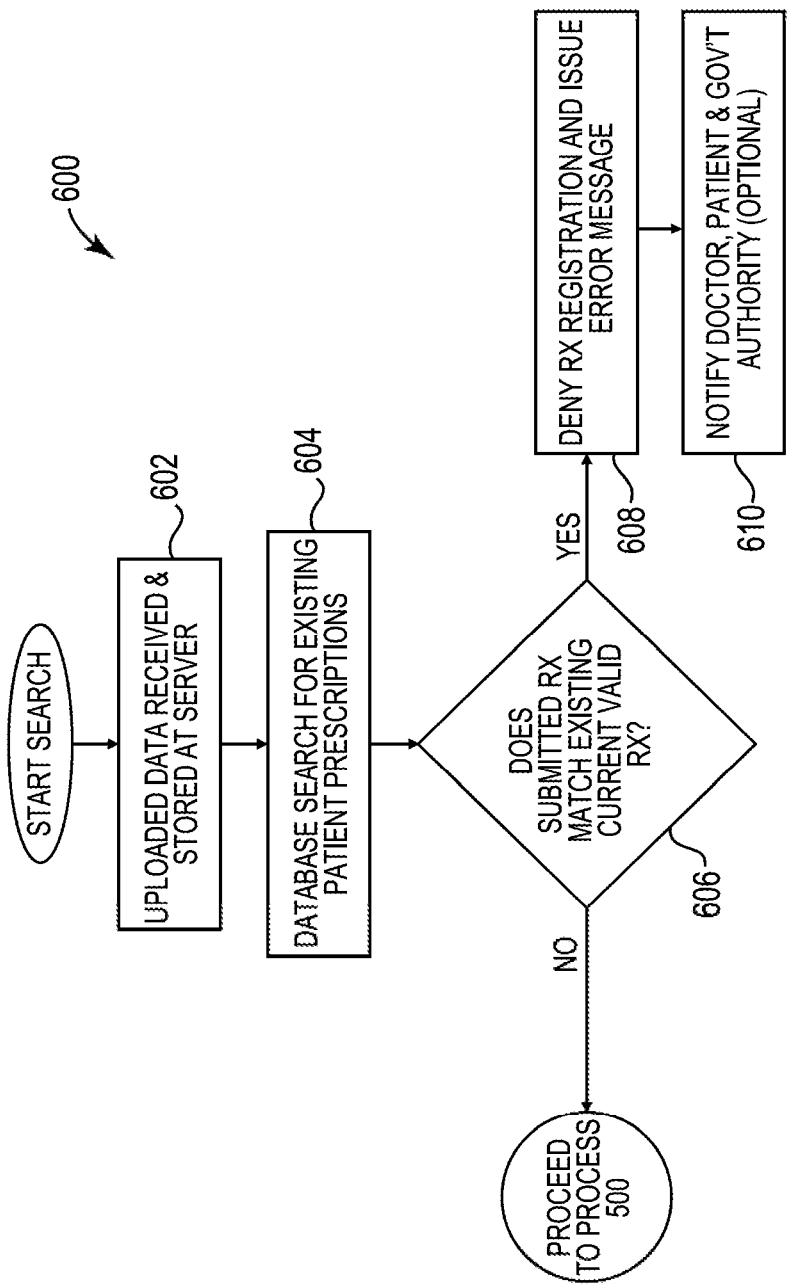
FIG. 6 is a flow diagram of a database search for existing prescriptions process in accordance with an embodiment of the present disclosure.

FIG. 6 is a flow diagram of a database search process 600 in accordance with an embodiment of the present disclosure. The process 600 may be an example search for existing prescriptions, but the process 600 may be implemented to search the system 10 for any number of parameters. At step 602, a user may upload or enter patient prescription information into a prescription management system, such as the system 10. The system may then proceed to step 604 in order to search a system database, such as the DB 45 and/or 50, for existing patient prescriptions. Additionally, the system may compare the uploaded prescription data with existing records to determine if for the patient under examination either a like prescription already exists or a possible drug interaction risk exists between the submitted prescription and the prescription being submitted. At step 606, the system may determine if a match is found. If the system yields a match with an existing prescription at the step 606, the system may proceed to step 608 to decline registration of the existing prescription and issues an error message. Optionally, at step 610 the system may notify an HCP's office, the patient and/or appropriate government entities. If no match is found at the step 606, the system may proceed to the prescription registration and generation of unique, separate and individual verification codes process 500 as discussed with regards to FIG. 5.

Figure 7:
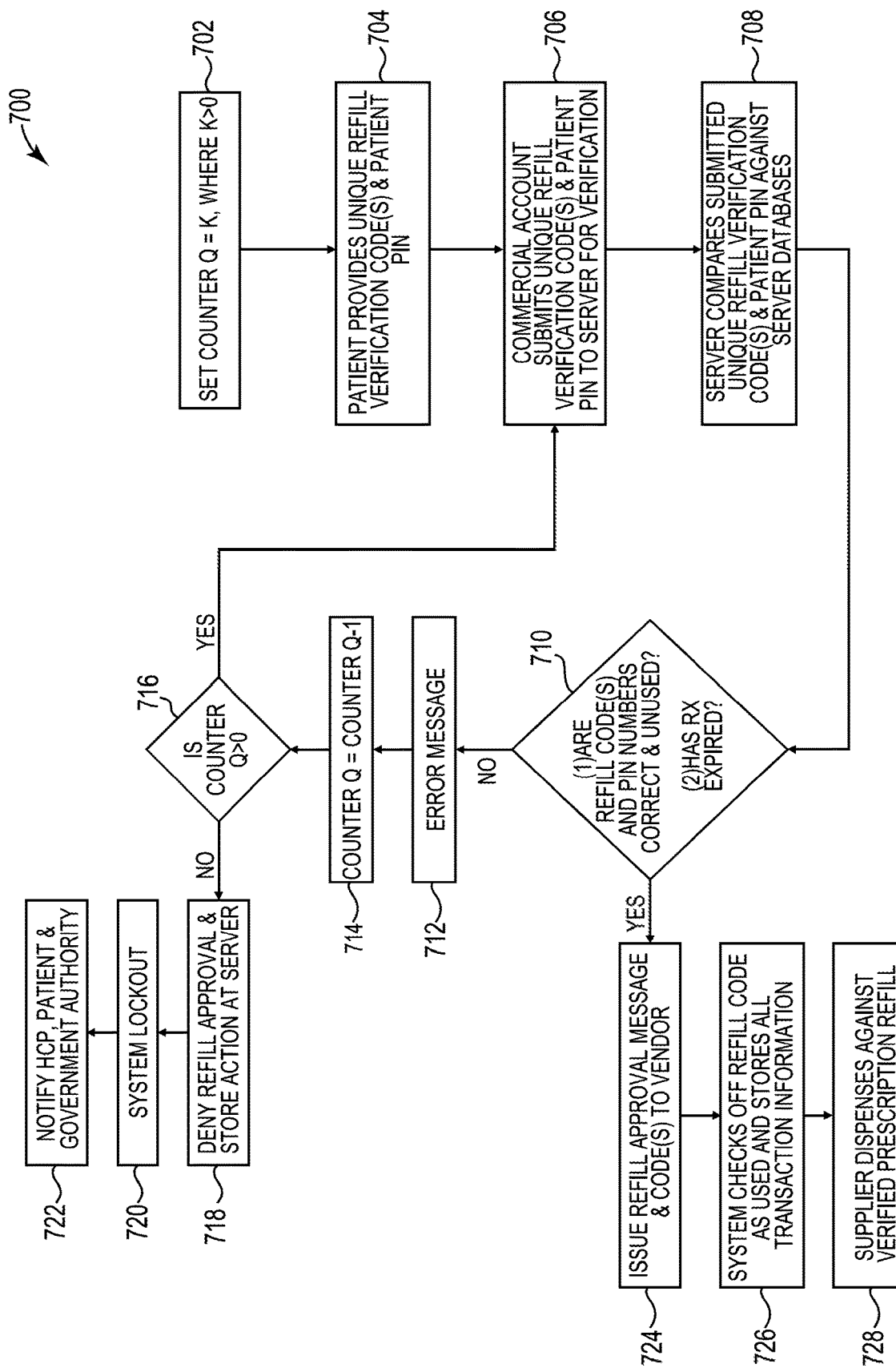
FIG. 7 is a flow diagram of a verification process for verifying individual, unique refill codes resulting in approval authorization in accordance with an embodiment of the present disclosure.

FIG. 7 is a flow diagram of a verification process 700 for verifying individual, unique refill codes resulting in approval authorization in accordance with an embodiment of the present disclosure. In accordance with the process 700, a pharmacy, dispenser or retailer registered with the system and accorded certain system prescription management authority may first perform the log-in process 400 of FIG. 4 in order to access a prescription management system, such as the system 10.

Upon successful login, a pharmacist, for example, may be given access to prescription refill management functions of the system. At step 702, the system may set a counter to a value of K, K being an integer number greater than zero. At step 704, a patient may present one or more unique, separate and individual refill verification codes along with the patient's PIN to the pharmacy, supplier, dispenser or retailer. In some embodiments, the patient may enter their PIN into an electronic keypad that is in communication with the system through the pharmacist's local device. Entry of the PIN via an electronic keypad may allow the patient to keep their PIN safe, e.g., private. The presentation of the patient's PIN and the unique, separate and individual refill verification codes, may allow the patient to select and unlock one or more particular prescription refills, authorize a particular dispenser or retailer to verify and to fill that refill(s), all while maintaining any other individual refills locked within the patient's account.

Whereas the order and manner of interacting with the prescription verification system may vary, completing the verification of a unique, separate and individual prescription refill verification code may require the entry and transmission of that refill verification code(s) and patient code associated with the particular patient identification provided by the patient to the commercial account of the pharmacist at step 706. At step 708, the system may compare the individual refill verification code(s) against the patient identification information. At step 710, the system may further determine if the refill code(s) and PIN are correct and whether the refill code(s) is an unused code. The system may also determine if the prescription has expired. If one or more of these values do not match those within the system's database(s), or if the prescription has expired, then the verification may not proceed. The system may then send an Error Message to the local device according to step 712. At step 714, the counter may be decreased by one, and the system may proceed to step 716 in order to compare the new value of the counter to the value of zero. If the new counter value is greater and zero, the system may prompt the pharmacist to resubmit the verification code(s) at step 706. If, however, the new counter value is determined to be equal to or less than zero, the system may deny verification and approval of the transaction and may proceed to step 718 in order to store the results at the server 22. The system may optionally initiate a system lockout at step 720, which may prevent further interaction with the system. The system may also notify the prescribing HCP, the HCP's office, the patient and/or appropriate government entities of the unsuccessful attempts to verify a separate, individual prescription refill and/or the attempt at prescription fraud at step 722.

If the server determines at step 710 that the prescription has not expired and that the individual refill verification code matches the system information, the system may approve the prescription refill as verified and may send to the user a verification message and approval code(s) at step 714. The system may then check-off, e.g., remove or flag as used, the valid verification code from the prescription code vector so that that particular code cannot again be used, and the appropriate pointer within the system may be reset to the next available code or codes within the prescription verification code vector at step 726. The pharmacy, dispenser or supplier may then dispense product(s) against the verified prescription and the verified particular unique, separate and individual refill verification code at step 728.

Figure 8:
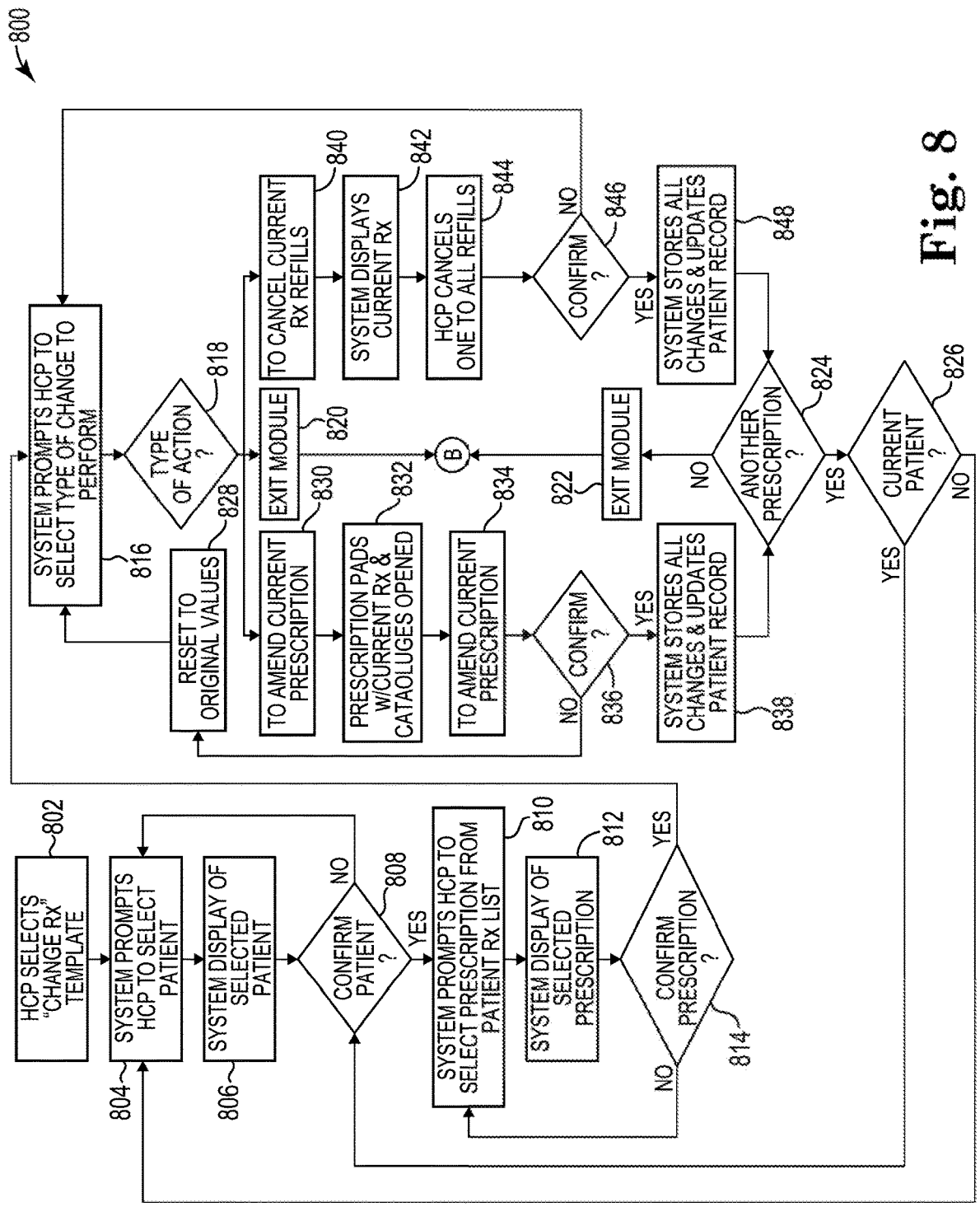
FIG. 8 is a flow diagram of a process used for accessing and managing prescriptions in accordance with an embodiment of the present disclosure.

FIG. 8 is a flow diagram of a process 800 used for accessing and managing prescriptions in accordance with an embodiment of the present disclosure. The process 800 may be used, for example, by an HCP to manage prescriptions for one or more patients. The process may be used to access one or more prescription management tools of a prescription management system that may enable HCPs to manage prescriptions after issue. In some instances, a follow-on medical exam subsequent to prescription issue may lead the HCP to advise the patient to discontinue using what was previously prescribed. However, any unfilled prescription refills may still remain and be treated as valid by a pharmacy. The patient may desire to continue taking the medication against doctor's advice, and could legitimately process the remaining refills. The system may remedy this unintended consequence by empowering HCPs with one or more retroactive prescription management tools.

Upon successful authentication and login by a user in accordance with the process 400 of FIG. 4, a user may be prompted with an array of tools, such as a change prescription tool. Initially, at step 802 an HCP may select the change prescription tool. At step 804, the system may prompt the HCP to select a particular patient from those for whom the doctor has registered a prescription. Upon the doctor choosing the patient, the system may proceed to step 806 in order to display the patient name, and at step 808, the system may prompt the user to confirm the displayed patient as the individual for whom a prescription modification is desired. If the displayed name is not the particular patient for whom the prescription change is intended, the system may return the user to step 804 in order to select a different patient name. Upon user confirmation to the system of the patient name at step 808, the system may proceed to step 810 to prompt the user to select the particular prescription which requires adjustment. Upon selection of the to-be-changed prescription from the list of prescriptions associated with the selected patient at step 810, the system may proceed to step 812 to display the particular prescription chosen for adjustment. The system may then proceed to step 814 in order to prompt the user to confirm the prescription choice. If the prescription selected is not confirmed, the system may return the user to step 810 so the user may reselect a prescription to be amended. If the user confirms the choice of prescription for amendment at step 814, the system may proceed to steps 816 and 818 to prompt the user to select the type of action desired to change the prescription. The types of actions may include, but is not limited so, to amend particular parameters comprising the existing prescription at step 830, or to cancel the prescription including one, several or all of the remaining refills at step 840. At step 820, the system may also allow for system exit.

Proceeding to step 830 to amend but not cancel a current prescription or any of its remaining refills may open a prescription pad template. At step 832, the system may populate the appropriate fields with existing values for each parameter comprising the prescription. The doctor may then change the existing prescription at step 834. Examples of such a change may be to change the prescribed dosage from one value to another value, to change the frequency of usage, to change the number of refills, to change the date of expiry and like changes. If the number of refills is increased to the current prescription or if the prescription itself is otherwise renewed, at time of uploading of these changes, the system may initiate generation of new verification codes in association with the new or additional refills.

Upon completion of the prescription changes, the system may prompt for confirmation of the prescription and its changes at step 836 before the altered prescription may be submitted to the server for registration. If the doctor declines to confirm, at step 828 the system may clear the prescription pad template of any changes and reset all parameter to their original values. The system may then prompt the doctor to choose an action concerning the selected prescription in accordance with the steps 816 and 818. Upon confirmation of the prescription and its changes at the step 836, the changed prescription may be submitted to the system (along with the doctor's e-signature). At step 838, the system may store all changes to the prescription, updates the patient record, records into the patient's prescription log both the access and change to the prescription, and notifies the patient of the changes.

At step 824, the system may allow the doctor to amend another prescription. If the doctor chooses to amend another prescription, the system may first verify if the doctor wishes to continue working with prescriptions for the same patient at step 826. If the same patient is selected, the system, at the step 808, may prompt the doctor to confirm this patient selection. If the doctor wishes to select a different patient, at the step 804, the system may prompt the doctor to select a patient from the patient list. Upon selection and confirmation of the patient whose prescription is to be changed, the system may be reset and the doctor may be prompted to select the prescription to change at the step 810. If, however, no further prescription changes are desired at the step 824, the user may exit the module at step 822.

Alternatively, the doctor may opt to cancel an existing prescription at the steps 816 and 818, which may cause the user to proceed to step 840. Upon the doctor's selection of this option at the step 840, the system may display the original prescription at step 842. At step 844, the system may prompt the user to select either the entire prescription with all refills or one or more of the remaining refills for cancellation. If the user declines to confirm the cancellation(s) at step 846, the system may send the user back to the step 816. If, however, the user confirms the cancellation(s) at the step 846, the confirmation, along with the doctor's e-signature, may be submitted to the system. The system may then make all appropriate cancellation changes to the existing prescription record, stores the transaction and transaction data, updates the patient record, removes the authentication numbers from the patient prescription, and notifies the patient of the cancellation(s) at step 848. The system may then allow the user to restart the process at either step 810, or at step 808. Else, the user may exit the prescription management tool at the step 822.

Additionally, the system enables the doctor not only to cancel an existing prescription or its refills, but also to make changes to application directions including that of ceasing all dosing using an existing medication currently in a patient's possession; notification of these changes would be automatically made to the patient or patient's guardian or caregiver, as well as being updated in the patient's prescription log. Changing dosing instructions may be performed by selecting the amend current prescription option at step 830.

FIG. 9 is an example prescription record 900 in accordance with an embodiment of the present disclosure. The record 900 may be an example of a general prescription that bear system-generated unique, separate and individual prescription refill verification codes for a pharmaceutical as generated by a prescription management system, such as the system 10. A relational database management system may generate the unique identification code 902 automatically per prescription. It may a standard index code or marker that allows for distinguishing between any two or more prescriptions within the system. The UKN vector 904 may include UKNs generated by the system and uniquely associated with a particular account and a particular UKD. The individual refill verification Codes 906 may contain the individual refill verification codes 906 for each refill of the associated prescription. The individual refill verification codes 906 may be generated as a composite of known parameters, which may include combinations of a user's UKN 904, doctor codes, the Unique ID Code for that prescription, prescription descriptive information, patient information or other parameters. For example, the individual refill verification codes 906 may have been generated for a pharmaceutical product by combining successive entries from the UKN vector 904 and an internal system code for oxycodone hydrochloride, R23 for example.

Each refill may have one and only one verification code. Further, each verification code may be unique from the other verification codes for a particular prescription and from all other verification codes for all other prescription refills within the system. In order to verify and dispense to a prescription's refill, each refill may be "unlocked" by providing both the public-key verification code, e.g., the unique verification code and the private-key, e.g., the patient identifier, such as a PIN.

It should be recognized that the foregoing systems and processes have been described in a manner emphasizing the fundamental aspects of the invention and that commercial embodiments may include hosts of embellishments and cosmetic details that are not described herein without departing from the scope of the invention and claims herein. It should be noted that information and data exchanged between local devices and the system's servers can be in either digital or acoustic tone form. It should also be recognized that the foregoing systems and processes facilitate secure prescription management in a manner that was heretofore unavailable. The benefits to consumers and public health include: prescription portability, confidential access to prescription information, the ability to make direct purchases, minimizing prescription abuse, optional tracking of gray markets, reminders of the need to revisit the prescribing doctor, and the like.

Another optional aspect of the invention is the capturing of an audit trail for each patient or each prescription. Preferably, the audit trail or "log" would store the activity in a patient account, specifically including the time, date and origin of all attempted access to a prescription or purchase of a prescription product. Access to the log would be governed by the system logic to determine which registered users would have rights to read its content. It is presumed that no direct writing privileges would be established for any user for direct entry of information into the log itself.

It is also anticipated that a "guardian" status may be utilized to provide parents and legal guardians with access to the prescription records of their dependents. Whereas the system rights of a "guardian" may be identical to that of a "patient", the system allows for differences in these rights to be established.

Still further, a patient may set up their account to grant temporary emergency access to paramedics and emergency room staffs in order to facility emergency care should the patient or a guardian be unable or unavailable to provide the patient identification and PIN. As technology develops, it is anticipated that another personal identifier, such as a fingerprint or an eye scan, could be used as a substitute for the PIN. Furthermore, as is the case for Health Care Professionals, the Unique Key Device may serve to authenticate other system users, such as a patient, guardians, pharmacy, insurance provider, government entity, manufacturer, supplier, retailer and others.

An "encyclopedic view" of a prescription record means that the all of the patient's prescriptions or medical information can be viewed. Alternatively, the HCP may have only have rights to a "limited view" of certain aspects of the prescription record. For example, an HCP that is an optometrist may be prevented from viewing every prescription in the record, but is certainly able to view any prescription for eye care and perhaps shown a flag for the existence of any known relevant prescriptions or conditions that could warrant further questioning or testing of the patient.

The patient is able to grant HCPs access to his prescription record by providing the HCP with the relevant patient identification (e.g., name, social security number, and/or account number, etc.) and a personal identification number (PIN) that is private to the patient and patient-authorized HCPs.

The system may also provide a patient account with various user functions, such as an opportunity to change PINs and view a log of successful and unsuccessful attempts to access the patient's prescription record. Optionally, the log may detail the scope of the HCP's review that was made during the access. Still further, the patient may set up automatic email notifications upon the occurrence of certain user-defined activity in the patient prescription record. For example, such activity might include any access requests, only successful accesses, or only accesses that view a certain medical condition or prescription.

While the foregoing is directed to examples of the present invention, other and further embodiments of the invention may be devised without departing from the basic scope thereof.

The invention claimed is:

1. A method for securing prescription data, the method comprising:
   generating a code vector including a series of authentication codes;
   storing at least one of the authentication codes on a peripheral device;
   maintaining an indication of a next expected authentication code from the code vector;
   allowing prescription creation by a user when the peripheral device is detected and determined to be an authorized device, and that the authentication code provided from the peripheral device matches the next expected authentication code;
   storing a prescription associated with a patient having a patient PIN, wherein the prescription is provided by the user;
   generating a plurality of refill verification codes associated with the prescription; and
   authorizing dispensing responsive to receipt of one of the plurality of refill verification codes and the patient PIN.

2. The method of claim 1, further comprising:
   after determining that the authentication code provided from the peripheral device matches the next expected authentication code, providing another one of the authentication codes from the code vector to the peripheral device; and
   removing the just substituted for authentication codes from the peripheral device.

3. The method of claim 2, further comprising:
   periodically requesting the authentication code from the peripheral device; and
   authenticating the periodically requested authentication code.

4. The method of claim 1, wherein generating a plurality of refill verification codes associated with the prescription comprises:
   determining one or more user parameters;
   determining one or more prescription parameters; and
   combining the one or more user and prescription parameters into a unique composite code or a series of codes.

5. The method of claim 1, wherein generating a code vector including a series of authentication codes comprises generating a series of random authentication codes based on one or more user parameters, and wherein the series of authentication codes are unique to the user and the peripheral device.

6. The method of claim 1, further comprising associating each of the plurality of refill verification codes with a respective refill of the prescription.

7. The method of claim 1, wherein authorizing dispensing responsive to receipt of one of the plurality of refill verification codes and the patient PIN, comprises:
   authenticating the PIN;
   authenticating the refill verification code;
   determining whether there are refills available for the prescription; and
   determining whether a date of expiry of the prescription has been reached.

8. A system for securing prescription data, the system comprising:
   one or more processing units; and
   at least one computer readable media encoded with instructions that, when executed, cause the one or more processing units to:
      generate a series of authentication codes;
      store at least one of the authentication codes on a peripheral device;
      maintain an indication of a next expected authentication code;
      allow prescription creation by a user when the peripheral device is detected and determined to be an authorized device, at least in part, by identifying a match between the next expected authentication code and the at least one authentication code provided by the peripheral device;
      store a prescription associated with a patient having a patient PIN, wherein the prescription is provided by the user;
      generate a plurality of refill verification codes associated with the prescription; and
      authorize dispensing responsive to receipt of one of the plurality of refill verification codes and the patient PIN.

9. The apparatus of claim 8, wherein the series of authentication codes are generated based on an associated user's personal information.

10. The apparatus of claim 8, wherein the instructions that cause the one or more processing units to generate a plurality of refill verification codes associated with the prescription, include further instructions that cause the one or more processors to:
   access the at least one of the authentication codes on the peripheral device;

access a prescription code associated with the prescription;

access personal information associated with the patient; and generate the plurality of refill verification codes based on a random combination of at least the at least one of the authentication code, the prescription code, the personal information or other variables.

11. The apparatus of claim 8, wherein the at least one computer readable media is encoded with further instructions that, when executed, cause the one or more processing units to:

provide the peripheral device with a next-in-line authentication code from the series of authentication codes; and remove the at least one authentication code from the series of authentication codes.

12. The apparatus of claim 8, wherein the at least one of the authentication codes stored on the peripheral device is periodically authenticated and updated.

13. The apparatus of claim 8, wherein to authorize dispensing responsive to receipt of one of the plurality of refill verification codes and the patient PIN, further comprises:

determine if the one of the plurality of refill verification codes is valid;

determine if the patient PIN is valid; and determine if the prescription is valid and that prescription's date of expiry has not been reached.

* * * * *